United States Patent
Ochiai et al.

(10) Patent No.: US 9,174,411 B2
(45) Date of Patent: Nov. 3, 2015

(54) LAMINATED SHEET AND PROCESS FOR PRODUCING THE SAME

(75) Inventors: Toru Ochiai, Okayama (JP); Shinichi Shigeki, Okayama (JP); Sumito Kiyooka, Okayama (JP); Ikuhisa Shiraishi, Saijo (JP); Nobuo Araya, Chiyoda-ku (JP)

(73) Assignee: KURARAYKURAFLEX CO., LTD., Okayama-shi (JP)

( * ) Notice: Subject to any disclaimer, the term of this patent is extended or adjusted under 35 U.S.C. 154(b) by 0 days.

(21) Appl. No.: 13/382,747

(22) PCT Filed: Jul. 7, 2010

(86) PCT No.: PCT/JP2010/061518
§ 371 (c)(1),
(2), (4) Date: Jan. 6, 2012

(87) PCT Pub. No.: WO2011/004834
PCT Pub. Date: Jan. 13, 2011

(65) Prior Publication Data
US 2012/0107387 A1  May 3, 2012

(30) Foreign Application Priority Data
Jul. 7, 2009 (JP) .................. 2009-160917

(51) Int. Cl.
*B32B 29/00* (2006.01)
*B32B 37/00* (2006.01)
(Continued)

(52) U.S. Cl.
CPC ............ *B32B 5/26* (2013.01); *A61K 8/0208* (2013.01); *A61Q 19/00* (2013.01); *B32B 5/022* (2013.01);
(Continued)

(58) Field of Classification Search
USPC ................................. 424/400, 402
See application file for complete search history.

(56) References Cited

U.S. PATENT DOCUMENTS 6,573,204 B1 6/2003 Philipp et al.
2005/0148261 A1 7/2005 Close et al.
(Continued)

FOREIGN PATENT DOCUMENTS

DE 100 44 694 A1 3/2002
EP 1 813 167 A1 8/2007
(Continued)

OTHER PUBLICATIONS

Hasui et al. JP 2007-070347, Mar. 22, 2007, English translation (PTO 13/0808).*

(Continued)

*Primary Examiner* — Gina Justice
(74) *Attorney, Agent, or Firm* — Oblon, McClelland, Maier & Neustadt, L.L.P.

(57) ABSTRACT

A laminated sheet is produced by forming an adhesion layer permeable to a liquid component and contactable with a skin on at least one side of a liquid-retention layer comprising a nonwoven structural member and having an ability to absorb the liquid component. The adhesion layer comprises a nonwoven structural member comprising a fiber having a number-average fiber diameter of not more than 10 μm, and the thickness ratio of the adhesion layer relative to the liquid-retention layer is 1/4 to 1/100 as a ratio of the adhesion layer/the liquid-retention layer. The fiber of the nonwoven structural member of the adhesion layer may have a standard deviation of fiber diameter of not more than 5. The nonwoven structural member of the liquid-retention layer may comprise a fiber having a fiber diameter larger than that of the fiber of the adhesion layer. The laminated sheet has a liquid retentivity and a liquid releasability in a well-balanced manner, and has an excellent adhesion and an excellent fit to the skin in the state where the sheet is impregnated with a liquid component.

18 Claims, 2 Drawing Sheets

(51) Int. Cl.
  *B32B 5/26* (2006.01)
  *D04H 1/4374* (2012.01)
  *D04H 1/4382* (2012.01)
  *D04H 1/492* (2012.01)
  *D04H 1/498* (2012.01)
  *A61Q 19/00* (2006.01)
  *A61K 8/02* (2006.01)
  *B32B 5/02* (2006.01)
  *B32B 5/08* (2006.01)

(52) U.S. Cl.
  CPC ............... *B32B 5/08* (2013.01); *D04H 1/4374* (2013.01); *D04H 1/4382* (2013.01); *D04H 1/492* (2013.01); *D04H 1/498* (2013.01); *B32B 2260/021* (2013.01); *B32B 2262/0223* (2013.01); *B32B 2262/0276* (2013.01); *B32B 2262/0284* (2013.01); *B32B 2262/0292* (2013.01); *B32B 2262/04* (2013.01); *B32B 2262/062* (2013.01); *B32B 2307/726* (2013.01); *B32B 2307/728* (2013.01); *Y10T 442/608* (2015.04)

(56) References Cited

U.S. PATENT DOCUMENTS

2006/0263322 A1* 11/2006 Konno et al. ............. 424/70.15
2008/0069845 A1   3/2008  Makihara et al.
2009/0238849 A1   9/2009  Iwata et al.

FOREIGN PATENT DOCUMENTS

| JP | 2006 110796 | 4/2006 |
| JP | 2007 070347 | 3/2007 |
| JP |    3944526  | 7/2007 |
| JP | 2009-97120 A | 5/2009 |
| JP | 2009 256856 | 11/2009 |
| WO | 2006 018969 | 2/2006 |

OTHER PUBLICATIONS

International Search Report issued on Oct. 5, 2010 in PCT/JP10/061518 filed on Jul. 7, 2010.
Extended European Search Report issued Nov. 28, 2013 in Patent Application No. 10797145.9.

* cited by examiner

LAMINATED SHEET AND PROCESS FOR PRODUCING THE SAME

TECHNICAL FIELD

The present invention relates to a laminated sheet which has an ability to absorb a liquid component (a liquid compound or composition) and is to be applied to the skin, and a process for producing the sheet, particularly relates to a laminated sheet which is to be impregnated with a liquid composition containing a beauty component or a medicinal component or other components and is to be attached to the skin (a living-body application sheet for liquid impregnation), and a process for producing the sheet.

BACKGROUND ART

As a conventional sheet for attachment to the skin of the human body or others, a skin care sheet impregnated with a liquid such as a cosmetic preparation (a liquid-impregnated sheet for living-body application) is being used. The skin care sheet as typified by a facial mask sheet simply allows the skin to be maintained in a highly wet or moist state, and a wide variety of commercial products is now being developed. As a material for the sheet, a woven fabric or a nonwoven fabric, each comprising (or made of) a fiber, is usually employed, and the nonwoven fabric is widely used because of costs. A spunlace nonwoven fabric comprising a cellulose-series fiber (as typified by a cotton having a high hydrophilicity) as a main component is often used as a nonwoven fabric sheet for impregnation with a cosmetic preparation. However, the spunlace nonwoven fabric of the cellulose-series fiber causes irritation to the skin and has an insufficient fitting property (or application property) to the skin.

Japanese Patent No. 3944526 (Patent Document 1) discloses a living-body application sheet for liquid (such as cosmetic preparation) impregnation, wherein an ultrafine fiber is present on a surface of the sheet in order to reduce the irritation to the face and improve the fitting property (or application property) to the face, specifically a skin application sheet for cosmetic preparation impregnation, wherein an ultrafine fiber layer which comprises at least 10% by mass of an ultrafine fiber with a fineness of at most 0.5 dtex and is placed on one surface or both surfaces of a hydrophilic fiber layer which comprises at least 50% by mass of a hydrophilic fiber, the hydrophilic fiber layer and the ultrafine fiber layer are integrated, and the ultrafine fiber layer is to be the surface which contacts with the skin. This document discloses that the ratio of the hydrophilic fiber is 10 to 70 parts by mass (preferably 15 to 50 parts by mass) relative to 100 parts by mass of the application sheet.

For a skin care sheet (a sheet for cosmetic preparation impregnation), it is necessary to combine capacities to retain and release a cosmetic liquid, although the application sheet has a difficulty in the compatibility between the liquid retentivity and the releasability. Further, the document is silent on the fiber diameter distribution of the ultrafine fiber. Moreover, in the case of a process for forming a nonwoven fabric by splitting a splittable conjugate fiber, it is difficult to obtain a nonwoven fabric comprising uniformly and moderately entangled fibers, the resulting nonwoven fabric has a low adhesion to the skin, causes irritation to the skin, and is less comfortable to wear. For example, the nonwoven fabric is often scratchy or unpleasant to the touch. In particular, when the nonwoven fabric is impregnated with a liquid component and contacted with (or applied to) the skin, the adhesion of the impregnated nonwoven fabric to the skin is insufficient. For example, when the fabric is left on the skin for a long time, the fabric often peels off or slips off the skin. In particular, since a sheet impregnated with a cosmetic preparation or others is used for the purpose of permeating the cosmetic preparation or others into the skin, the sheet requires a capability to adhere to the skin over a wider area for a long time in use. The peeling-off or slipping-off due to a low adhesion of the sheet discomforts or dissatisfies a user. When the sheet is also used as a kind of amenity product, which is pleasant or comfortable, the sheet requires less irritation and higher adhesion to the skin to give a user a feeling of satisfaction. In addition, the comfort (or satisfaction) produced by a long-lasting high adhesion of the sheet is a key factor in evaluating a commercial value. Moreover, in response to the changes in society, the sheet for cosmetic preparation impregnation is being used in many different situations or states. For example, for working women, since it is difficult to spare their precious time for skin care, such women use the sheet in a straighten up position (or with the upper part of the body elevated) to no small extent, e.g., while doing housework, watching TV, or reading books. Accordingly, there is a demand for a sheet for cosmetic preparation impregnation, having a higher adhesion and a higher liquid-retention (liquid-holding capacity).

Further, the sheet for impregnation with a cosmetic preparation is being used in order to not only achieve an efficacy on the skin of an active component contained in a liquid (liquid component) but also produce a comfort (or a good feeling) in use, and the comfort is a factor of inciting buying inclination. Thus the sheet is also worth using as an amenity product. This is a reason for a recent increasing demand for the sheet. Specifically, a desired sheet has a soft "feel" against the skin and provides both the feeling that the skin is fully covered with a liquid coat of a cosmetic preparation and the "adhesion feeling" as clung to the skin for a long time.

In particular, a demand for a sheet impregnated with a cosmetic preparation or others, as typified by a facial mask sheet, is now being increased, and accordingly a sheet having a higher performance and a greater comfort is required. The sheet is primarily used to keep the skin highly wet (or moist) during use with various cosmetic preparations each having different effects. Accordingly, it is necessary for the sheet to have a liquid retention suitable for keeping the skin highly wet (or moist).

RELATED ART DOCUMENTS

Patent Documents

Patent Document 1: JP-3944526B

SUMMARY OF THE INVENTION

Problems to be Solved by the Invention

It is therefore an object of the present invention to provide a laminated sheet having a liquid retentivity and a liquid releasability in a well-balanced manner, as well as having an excellent adhesion and an excellent fit (or conformity) to the skin in the state where the sheet is impregnated with a liquid component; and a process for producing the sheet.

Another object of the present invention is to provide a laminated sheet which has a soft feel against the skin and provides both the feeling that a liquid component (e.g., a cosmetic preparation) applied to the skin is spread to the whole of the applied skin and the adhesion feeling for a long time; and a process for the producing the sheet.

It is still another object of the present invention to provide a laminated sheet having less slipping-off or peeling-off from the skin when used as a skin care sheet (e.g., a facial mask sheet) even for a long time; and a process for producing the sheet.

Means to Solve the Problems

The inventors of the present invention made intensive studies to achieve the above objects and finally found that an adhesion layer comprises a nonwoven structural member comprising a fiber having a number-average fiber diameter of not more than 10 μm is laminated on at least one side of a liquid-retention layer comprising a nonwoven fabric (a nonwoven structural member), where the thickness of the adhesion layer is smaller than that of the liquid-retention layer, to give a laminated sheet having a liquid retentivity and a liquid releasability in a well-balanced manner and an improved adhesion and fit to the skin. The present invention was accomplished based on the above findings.

That is, the laminated sheet of the present invention comprises a liquid-retention layer which comprises a nonwoven structural member (a first nonwoven structural member) comprising a first fiber and has an ability to absorb a liquid component, and an adhesion layer contactable with a skin, the adhesion layer being formed on at least one side of the liquid-retention layer and being permeable to the liquid component, wherein the adhesion layer comprises a nonwoven structural member (a second nonwoven structural member) comprising a second fiber, and the second fiber has a number-average fiber diameter of not more than 10 μm, and the thickness ratio of the adhesion layer relative to the liquid-retention layer is 1/4 to 1/100 as a ratio of the adhesion layer/the liquid-retention layer. The second fiber may have a standard deviation of fiber diameter of not more than 5. The first fiber may have a fiber diameter larger than that of the second fiber. The first fiber may comprise a hydrophilic resin fiber, and the second fiber may comprise a thermoplastic resin fiber. The first fiber may comprise a hydrophilic resin fiber in a proportion of less than 50% by mass of the liquid-retention layer. The second fiber may comprise at least one member selected from the group consisting of a polyester fiber, a polyolefin fiber, a poly(vinyl alcohol)-series fiber, and a polyurethane fiber. The first fiber (the fiber constituting the liquid-retention layer) may have a number-average fiber diameter of 9 to 32 μm. The second fiber (the fiber constituting the adhesion layer) may have a number-average fiber diameter of 1 to 8 μm. The liquid-retention layer may have a density of 0.03 to 0.20 g/cm$^3$ and a void (or gap) ratio of not less than 80%, and the adhesion layer may have a density of 0.05 to 0.35 g/cm$^3$ and a void ratio of not less than 70%. The adhesion layer may comprise a meltblown nonwoven fabric. The laminated sheet of the present invention may have a stress at 50% elongation of about 0.5 to 15 N/5 cm in at least one direction under wetting in accordance with JIS (Japanese Industrial Standards) L 1913. The laminated sheet of the present invention may be a sheet impregnated with a liquid component. The laminated sheet of the present invention may be a skin care sheet (in particular, a facial mask sheet) containing a cosmetic preparation as the liquid component. The laminated sheet of the present invention may further comprise another adhesion layer or a nonporous film formed on the liquid-retention layer. The laminated sheet of the present invention may have a frictional force of not less than 0.6 N when the sheet is impregnated with 500% by mass of a cosmetic preparation relative to the mass of the sheet, and the frictional force of the sheet impregnated with 500% by mass of the cosmetic preparation may be larger than that of a sheet impregnated with 900% by mass of the cosmetic preparation relative to the mass of the sheet, wherein the frictional force of each impregnated sheet is measured in accordance with ASTM-D1984.

The present invention also includes a process for producing the laminated sheet, which comprises a step for forming an adhesion layer by a meltblown method, and a step for laminating the adhesion layer on at least one side of a liquid-retention layer comprising a nonwoven structural member. In the production process, the liquid-retention layer may be produced by entangling a hydrophobic fiber and a hydrophilic fiber by a spunlace method, and the lamination step may comprise entangling the liquid-retention layer and the adhesion layer by a spunlace method or directly blowing a fiber for the adhesion layer to the liquid-retention layer. Moreover, in the production process, the liquid-retention layer may be produced by entangling and thermally bonding a hydrophobic fiber and a hydrophilic fiber containing an ethylene-vinyl alcohol copolymer under moisture by a steam jet method, and the lamination step may comprise entangling the liquid-retention layer and the adhesion layer by a spunlace method or directly blowing a fiber for the adhesion layer to the liquid-retention layer.

The present invention includes a using method of the laminated sheet, which comprises allowing the adhesion layer to contact with a skin, wherein the laminated sheet has been impregnated with a liquid component.

As used herein, the term "skin care" means not only the use of a cosmetic preparation, a milky lotion, and the like to look after the skin (typical skin care) but also wider concepts including other actions which can be associated with the skin. Thus the skin care sheet (or sheet for skin care) may include, for example, a sheet to be applied (or touched) to the skin, e.g., a sheet for washing the skin, a sheet for relieving an skin itching, a sheet for cooling through the skin, and a sheet for reducing an inflammation and other symptoms by penetration (or infiltration) in the skin (e.g., a compress).

Effects of the Invention

The sheet of the present invention comprises a liquid-retention layer and an adhesion layer laminated on at least one side of the liquid-retention layer, the liquid-retention layer comprises a first nonwoven structural member, and the adhesion layer comprises a second nonwoven structural member comprising a fiber having a number-average fiber diameter of 10 μm, where the thickness of the adhesion layer is smaller than that of the liquid-retention layer; and the sheet has a liquid retentivity and a liquid releasability in a well-balanced manner, and excellent adhesion and fit to the skin in the state in which the sheet is impregnated with a liquid component. Moreover, the uniform adjustment of the fiber diameter of the fiber in the adhesion layer imparts flatness and smoothness to the surface of the adhesion layer, and the sheet impregnated with a liquid component has an improved adhesion and fit to the skin. Further, the sheet has a soft feed against the skin (or is soft to the touch) and provides for a long time both the feeling that a liquid component (e.g., a cosmetic preparation) applied to the skin is spread to the whole of the applied skin and the adhesion feeling. Furthermore, even use of the sheet as a skin care sheet (e.g., a facial mask sheet) for a long time has less slipping-off or peeling-off from the skin. In particular, since the adhesion layer comprises a meltblown nonwoven fabric comprising an ultrafine fiber and the distance between the liquid-retention layer and the skin is extremely short, the contact of the fiber with the skin causes extremely small scratchy irritation. The liquid coat formed at the interface between the adhesion layer and the skin is extremely strong compared with existing techniques, and the sheet achieves a sufficient skin adhesion to give a comfort level to a user.

DESCRIPTION OF EMBODIMENTS

Figure 1:
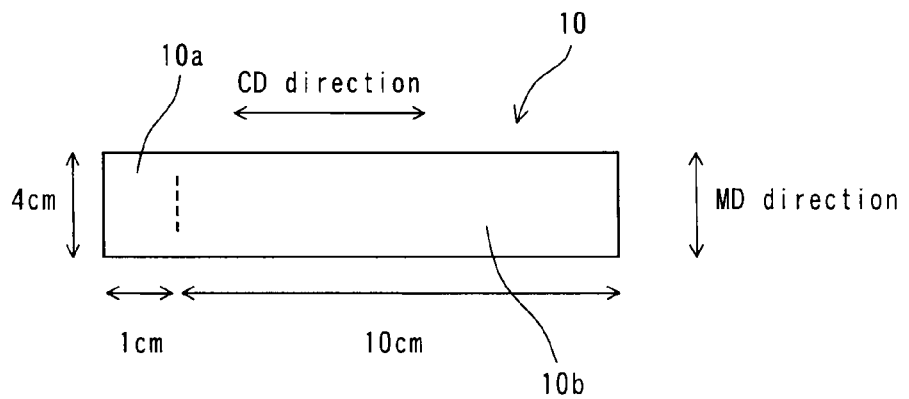
FIG. 1 is a schematic plan view of a sample for an adhesion test.

The laminated sheet of the present invention comprises a fabric and has a structure comprising a liquid-retention layer and an adhesion layer, where the liquid-retention layer has an ability to absorb a liquid component, and the adhesion layer is formed on at least one side of the liquid-retention layer, is permeable to the liquid component (a liquid effective component (or ingredient)), and is contactable with a skin. That is, the laminated sheet (a living-body application sheet for liquid impregnation) of the present invention comprises a liquid-retention layer for impregnating a liquid component and an adhesion layer located at a side directly contacting with the skin.

[Liquid-Retention Layer]

According to the present invention, the liquid-retention layer has a wettability necessary to impregnate a liquid component (liquid compound or composition) containing a beauty component or a medicinal (effective) component [for example, a moisturizing component, a cleansing component, an antiperspirant component, an aroma (or fragrance) component, a whitening (or skin-lightening) component, a blood-circulation-promoting component, a cooling component, an ultraviolet-ray-absorbing component, and an anti-itch component for skin] and voids for retaining (or holding) the liquid component. When handled, the liquid-retention layer retains (or holds) the liquid component without dripping from the layer until a predetermined site of the body (e.g., the face) is covered with the sheet. The laminated sheet is attached to or laid on the skin, and then the liquid-retention layer plays a role in gradually allowing to move (or transfer) the liquid composition toward the adhesion layer, which is contactable with the skin.

The liquid-retention layer having such characteristics may usually comprise a woven fabric or a nonwoven fabric or others. In view of the productivity and others, the nonwoven fabric (or nonwoven structural member) is preferred. Further, in order to ensure the wettability or the liquid retentivity, the nonwoven fabric for the liquid-retention layer preferably contains a fiber comprising a hydrophilic resin. When a liquid (such as a cosmetic preparation) is added to the sheet, the fiber comprising the hydrophilic resin plays an important role in incorporating the liquid into the inside of the fiber structure of the liquid-retention layer as well as retains (or holds) a large quantity of the incorporated liquid cosmetic preparation without dripping from the sheet in use (or handling).

Further, from the viewpoint of well-balanced liquid retentivity and liquid releasability, it is particularly preferable that the nonwoven fabric comprise a mixture (blended fibers) containing a hydrophilic resin fiber (a hydrophilic fiber) and a hydrophobic resin fiber (a hydrophobic fiber). The ratio of the hydrophilic fiber relative to the hydrophobic fiber (mass ratio) [the former/the latter] may be selected from about 99/1 to 1/99 and is, for example, about 90/10 to 10/90. When the ratio of the hydrophilic fiber is excessively small, the resulting unadaptability of the sheet to the liquid component causes an uneven liquid quantity in the sheet, a low capability of the sheet to retain the liquid component, or a dripping from the sheet in use. On the other hand, when the ratio of the hydrophilic fiber is excessively large, the capability of the sheet to retain the liquid component becomes high. Thus, since it is difficult to release the liquid cosmetic preparation toward the skin in use or an excessive quantity of the liquid component is needed beforehand to secure a necessary releasing quantity, the liquid component is often used wastefully.

Further, the ratio (mass ratio) of the hydrophilic fiber relative to the hydrophobic fiber [the hydrophilic fiber/the hydrophobic fiber] may be about 30/70 to 50/50 (mass ratio) from the viewpoint of balancing the induction of the liquid component to the inside of the fiber structure, the retention of the liquid component without dripping in handling, and the release of the liquid component toward the skin. Furthermore, from the viewpoint of the improvement in liquid releasability (e.g., the release of the liquid component toward the skin), the ratio of the hydrophilic fiber may be less than 50% by mass. For example, the ratio (the hydrophilic fiber/the hydrophobic fiber) may be about 5/95 to 45/55, preferably about 10/90 to 40/60, and more preferably about 10/90 to 30/70 (mass ratio). Thus, for the aqueous liquid component, the balance of the liquid retentivity and liquid releasability is improved by making the ratio of the hydrophobic fiber larger than that of the hydrophilic fiber.

The liquid-retention layer may have a layered structure composed of a plurality of layers with different fiber compositions. For example, when the sheet is used as a sheet for cosmetic preparation impregnation, or the like, an effect that a region near the skin becomes a wet (or moist) state more rapidly can be expected by increasing the ratio of the hydrophilic fiber in the region near the skin (that is, a region near the adhesion layer). Specifically, when the laminated sheet comprises the liquid-retention layer having a layer comprising the hydrophilic fiber in a higher ratio and located in a side near the skin, and is gently placed on (or laid on) the skin, the liquid component is moved toward the direction that the ratio of the hydrophilic fiber is higher in the liquid-retention layer and allows the skin side to be a high wet (moist) state in a short time. The liquid-retention layer may have a two-layer structure, for example, a structure composed of a first layer which is located at a front (or outer) side of the sheet and contains a hydrophilic fiber in a ratio of not more than 30% by mass (e.g., 10 to 30% by mass) and a second layer which is located at a side near the adhesion layer and contains a hydrophilic fiber in a ratio of not less than 70% by mass (e.g., 70 to 90% by mass).

The hydrophilic fiber is not particularly limited to a specific one as far as the fiber has a hydrophilicity. As the hydrophilic fiber, a synthetic fiber, a natural fiber, a regenerated fiber, and other fibers may be selected. The regenerated fiber is produced by dissolving a natural plant fiber or an animal protein fiber and then regenerating the dissolved matter with a chemical treatment. Further, it is sufficient that the hydrophilic fiber comprises a hydrophilic resin in at least a surface thereof. For example, the hydrophilic fiber may include a fiber in which a hydrophobic fiber is treated to impart hydrophilicity to a surface thereof, a conjugated fiber (or a conjugate fiber) comprising a core composed of a hydrophobic resin, and others.

The synthetic fiber may include, for example, a synthetic fiber which comprises a resin having a hydrophilic group such as a hydroxyl group, a carboxyl group, or a sulfonic acid group (particularly a hydroxyl group) in a molecule thereof [for example, a poly(vinyl alcohol)-series resin, a polyamide-series resin, or a polyester-series resin such as a poly(lactic acid); a (meth)acrylic copolymer containing a (meth)acrylamide unit; and others]. These synthetic fibers may be used alone or in combination. Among these synthetic fibers, a hydrophilic resin having a hydroxyl group in a monomer unit thereof is preferred. In particular, from the viewpoint of a uniform distribution of hydroxyl groups in a molecule, a fiber comprising an ethylene-vinyl alcohol copolymer is preferred.

For the ethylene-vinyl alcohol-series copolymer, the ethylene unit content (the ratio of the ethylene unit in the copolymer) is, for example, about 10 to 60 mol %, preferably about 20 to 55 mol %, and more preferably about 30 to 50 mol %. The saponification degree of the vinyl alcohol unit is, for example, about 90 to 99.99 mol %, preferably about 95 to 99.98 mol %, and more preferably about 96 to 99.97 mol %. The viscosity-average degree of polymerization is, for example, about 200 to 2500, preferably about 300 to 2000, and more preferably about 400 to 1500. As described later, a thermal adhesive resin under moisture (or moisteable-thermal adhesive resin, moisteable adhesive resin under heat, or adhesive resin under heat and moisture), such as an ethylene-vinyl copolymer, can be used to form a bulky and stable liquid-retention layer by a steam jet method.

Examples of the natural fiber may include a cotton, a silk, a flax (or a linen), a silk, and a wool. These natural fibers may be used alone or in combination. Among them, a cotton or the like is widely used.

The regenerated fiber may include, for example, a cellulose-series fiber such as a rayon (e.g., a viscose rayon), an acetate, Tencel such as a lyocell, a cupra, or a polynosic. These natural fibers may be used alone or in combination. Among them, a rayon fiber or a Tencel fiber is widely used.

Regarding the fiber of which a surface comprises a hydrophilic resin, a method for imparting a hydrophilicity to a surface of a fiber may include a method which comprises making a fiber-formable (or fiber-forming) resin and a hydrophilic resin into a fibrous form to cover at least a region of the fiber surface with the hydrophilic resin. A conjugated fiber formed by the method of covering the fiber surface with the hydrophilic resin is preferred because of less deterioration in hydrophilicity even when used for a long time. Moreover, the method of making a fiber-formable resin and a hydrophilic resin into a fibrous form is preferred in view of the shortening of the production process and the achievement of a uniformly high hydrophilicity. In particular, in the respect of a high hydrophilicity, it is preferred to use a fiber having a whole surface thereof covered with a hydrophilic resin in a sheath form, that is, a conjugated fiber having a sheath-core structure in which the sheath comprises a hydrophilic resin.

The sheath-core structure conjugated fiber is not particularly limited to a specific one as far as the sheath comprises a hydrophilic resin. The core preferably comprises a hydrophobic resin for the after-mentioned hydrophobic fiber in order to maintain the form (or shape) of the fiber even in the impregnation with the liquid component and prevent the determination of the permeability. Further, among the hydrophobic resins, for example, the preferred resin includes a polypropylene-series resin, a polyester-series resin, and a polyamide-series resin. In particular, in view of a well-balanced heat resistance, fiber-forming property, and the like, a polyester-series resin [e.g., a poly(ethylene terephthalate)] is preferred. Incidentally, in view of the production of a bulky and stable nonwoven fabric, or the others, the preferred hydrophilic resin for the sheath includes a resin for a synthetic fiber, particularly, a poly(vinyl alcohol)-series resin such as an ethylene-vinyl alcohol copolymer. For the sheath-core structure conjugated fiber, the ratio (mass ratio) of the core relative to the sheath [the sheath/the core] is, for example, about 90/10 to 10/90 (e.g., about 60/40 to 10/90), preferably about 80/20 to 15/85, and more preferably about 60/40 to 20/80.

Moreover, among these hydrophilic fibers, a cellulose-series fiber (e.g., a rayon and Tencel) is permeable to water or an aqueous solution, a polar solvent, or an emulsion thereof which constitute the liquid component (e.g., a cosmetic preparation) to the inside of the fiber and has an excellent absorbability and a high liquid retentivity. In these respects, the cellulose-series fiber is particularly preferred. On the other hand, an ethylene-vinyl alcohol copolymer fiber (particularly, a sheath-core structure conjugated fiber in which the sheath comprises an ethylene-vinyl alcohol copolymer) is inferior to the cellulose-series fiber in liquid retentivity. However, the ethylene-vinyl alcohol copolymer fiber has an excellent adaptability to the liquid component (e.g., a cosmetic preparation), the fiber itself does not absorb the liquid component, and the liquid component is easily released under a pressure or other means. In these respects, the ethylene-vinyl alcohol copolymer fiber is particularly preferred. Accordingly, the cellulose-series fiber and the ethylene-vinyl alcohol copolymer fiber may be selected depending on the viscosity or quantity of the liquid component (e.g., a cosmetic preparation). Further, the liquid retentivity and releasability may be controlled by mixing these fibers. Furthermore, if necessary, other fibers may be added to the fiber(s).

The hydrophobic fiber or nonhydrophilic fiber for the liquid-retention layer is used to obtain the structural stability of the liquid-retention layer. The nonhydrophilic fiber refers to a fiber having a polarity which is not so high and a relatively strong hydrophobicity.

The Young's modulus of the hydrophobic fiber hardly decreases even when the liquid-retention layer is in a wet (or moist) state. Thus the hydrophobic fiber performs to maintain the bulkiness or stiffness of the liquid-retention layer.

The hydrophobic fiber is not particularly limited to a specific one and may include a fiber which comprises a resin having an official regain of less than 2.0% in a standard state (20° C., 65% RH). Examples of the resin may include a resin commonly used for nonwoven fabric, e.g., a polyolefin-series resin (e.g., a polyethylene and a polypropylene), a polyester-series resin [e.g., a poly(ethylene terephthalate), a poly(butylene terephthalate), and a poly(ethylene naphthalate)], a polyamide-series resin (e.g., a polyamide 6, a polyamide 6,6, and a polyamide 4,6), a polyurethane-series resin (e.g., a polyesterpolyol-based urethane-series resin), and a polyacrylonitrile-series resin. These hydrophobic fibers may be used alone or in combination. Among them, in terms of high versatility, excellent mechanical properties, or others, a polyester fiber is preferred.

The fiber (the hydrophilic fiber and the hydrophobic fiber) for the liquid-retention layer may further contain a conventional additive, for example, a stabilizer (e.g., a heat stabilizer such as a copper compound, an ultraviolet absorber, a light stabilizer, and an antioxidant), a dispersing agent, a particulate (or fine particle), a coloring agent, an antistatic agent, a flame-retardant, a plasticizer, a lubricant, and a crystallization speed retardant. These additives may be used alone or in combination. The additive may adhere on (or may be supported to) a surface of the liquid-retention layer or may be contained in the fiber.

The cross-sectional form of the fiber (the hydrophilic fiber and the hydrophobic fiber) for the liquid-retention layer is not particularly limited to a specific one. For example, the cross-sectional form may includes various cross-sectional forms such as a circular form, a modified (or deformed) form (such as a flat form or an elliptical form), a polygonal form, a multi-leaves form (a 3- to 14-leaves form), a hollow form, a V-shaped form, a T-shaped form, an H-shaped form, an I-shaped form (dog-bone form), and an array form. Among them, a circular cross-sectional form, an elliptical cross-sectional form, or the like is widely used.

The length of the fiber for the liquid-retention layer is not particularly limited to a specific one. The fiber may be a staple fiber (or a short fiber). In order to obtain a dry nonwoven fabric by a carding process, the fiber preferably has a fiber length of 20 to 70 mm. In particular, a fiber having a fiber length of 25 to 60 mm is preferred due to an easy production of a web having a uniform fabric appearance in view of easy passage through a card. The fiber length may suitably be adjusted according to purposes.

The diameter of the fiber for the liquid-retention layer is preferably larger than that of the fiber for the adhesion layer in terms of mechanical properties or others. It is sufficient that the fiber diameter (number-average fiber diameter) is concretely not less than 5 μm in view of an excellent balance between the liquid retentivity and the liquid releasability. Considering a balance between the impregnation with the liquid component (e.g., a lotion) and the liquid retentivity of the liquid component, the fiber diameter is, for example, about 9 to 32 μm, preferably about 10 to 25 μm, and more preferably about 10 to 20 μm.

The basis weight of the nonwoven fabric (nonwoven structural member) for the liquid-retention layer is, for example, about 20 to 200 g/m$^2$, preferably about 25 to 150 g/m$^2$, and more preferably about 30 to 120 g/m$^2$ (particularly about 30 to 100 g/m$^2$). When the basis weight is excessively small, it is difficult to ensure a space for liquid retention between fibers. Moreover, when the basis weight is excessively large, the quantity of the liquid to be retained in the liquid-retention layer is excessively increased. As a result, a large quantity of the effective component stays in the liquid-retention layer without reaching the skin, and the effective component is often wasteful.

The density of the liquid-retention layer (the density of the liquid-retention layer in the laminated sheet) is, for example, about 0.03 to 0.20 g/cm$^3$, preferably about 0.05 to 0.17 g/cm$^3$, and more preferably about 0.1 to 0.15 g/cm$^3$ depending on the viscosity of the liquid component (e.g., a cosmetic preparation) for impregnation. A liquid-retention layer having an excessively low density deteriorates the liquid retentivity of the sheet and easily causes dripping of the liquid from the sheet in handling. On the other hand, a liquid-retention layer having an excessively high density decreases the quantity of the liquid to be retained, and additionally shows a tendency to slow down the movement speed of the liquid to the adhesion layer.

The void ratio of the liquid-retention layer (the void ratio of the liquid-retention layer in the laminated sheet) may for example be not less than 80% (e.g., 80 to 99%), preferably not less than 85% (e.g., 85 to 98%), and more preferably not less than 90% (e.g., 90 to 95%) in order to ensure the impregnation quantity of the liquid component (e.g., a cosmetic preparation).

The thickness of the liquid-retention layer may be selected from the range of about 100 to 3000 μm and is, for example, about 200 to 2000 μm, preferably about 300 to 1500 μm, and more preferably about 400 to 1200 μm (particularly about 400 to 1000 μm).

[Process for Producing Liquid-Retention Layer]

The nonwoven fabric or nonwoven structural member for the liquid-retention layer can be produced by a conventional method, for example, a spunlace method, a needle punch method, and a steam jet method. Among these methods, when the cost is considered as important, the spunlace method, by which the nonwoven fabric can be produced industrially at a high speed, may be used. In order to improve the liquid retentivity of the nonwoven fabric by increasing the bulkiness thereof, there may be used the thermal bonding method, the steam jet method, and others (particularly, the steam jet method, in terms of uniform bonding in the thickness direction and highly balanced form retentivity and bulkiness).

For the spunlace method, the staple fibers, for example, a hydrophobic fiber and a hydrophilic fiber, may be blended and opened by, e.g., carding with a carding machine to produce a nonwoven fabric web. The nonwoven fabric web may be produced by mixing the fibers constituting the web at the ratio and may be a parallel web (in which the fibers are arranged in a forward (or traveling) direction of a carding machine), a cross web (in which the parallel webs are cross-laid), a random web (in which the fibers are randomly arranged), or a semi-random web (which is intermediate between the parallel web and the random web). For the random web or the cross web, since the fibers are entangled with each other in the crosswise (or cross-machine) direction of the web to inhibit the stretch of the web in the crosswise direction, these webs have a tendency to decrease the conformity (or clinging property) to the skin in use. Accordingly, the parallel web and the semi-random web, which can ensure the softness and stretch in the crosswise direction of the webs, are preferred compared with the random web and the cross web.

Further, for the spunlace method, the resulting nonwoven fabric web is subjected to hydroentangling. In the hydroentangling, a high-pressure water flow spouted (or jetted) from a nozzle plate is led to collide with the nonwoven fabric web placed on a porous supporting member to three-dimensionally entangle the fibers of the nonwoven fabric web with each other and integrate the fibers; in which the nozzle plate has jet orifices drawn up (or arranged) in one to two lines, each orifices having a diameter of about 0.05 to 0.20 mm and a pitch of about 0.30 to 1.50 mm. When the nonwoven fabric web is subjected to the three-dimensional entanglement, it is preferable that the nonwoven fabric web placed on a moving porous supporting member be treated once or a plurality of times with a water flow at a water pressure of about 10 to 150 kg/cm$^2$ (≈1 to 15 MPa), preferably about 20 to 120 kg/cm$^2$ (≈2 to 12 MPa), more preferably about 30 to 100 kg/cm$^2$ (≈3 to 10 MPa). A preferred manner is as follows: the jet orifices are arranged in line in a direction perpendicularly to the traveling direction of the nonwoven fabric web, and the nozzle plate having the jet orifices arranged is vibrated in a direction perpendicular to the traveling direction of the nonwoven fabric web placed on the porous supporting member at the same width as the pitch of the jet orifices to lead the water flow to collide with the nonwoven fabric web uniformly. The porous supporting member for placing the nonwoven fabric web is not particularly limited to a specific one as far as the water flow can pass through the nonwoven fabric web. The porous supporting member may include, for example, a mesh screen (e.g., a wire mesh) and a punched (or perforated) board. The distance between the jet orifices and the nonwoven fabric web may be selected depending on the water pressure and is, for example, about 1 to 10 cm. When the distance is beyond this range, the resulting nonwoven fabric easily deteriorates the fabric appearance or has an insufficient three-dimensional entanglement of the fibers.

The nonwoven fabric web may be subjected to a drying treatment after the hydroentangling. As the drying treatment, first, it is preferable to remove excess water (or moisture) from the hydroentangled nonwoven fabric web. The removal of the excess water can be conducted by a known method. For example, the excess water may be removed using a squeezing machine (such as a mangle (mangle roll)) to a certain extent, and successively the remaining water may be removed using a dryer such as a suction-band type hot-wind circulation dryer.

For the steam jet method, the fibers of the resulting nonwoven fabric web may be entangled with each other by spraying the web with a high-temperature water vapor (high-pressure steam) to form an adhesion layer. For the steam jet method, in addition to entanglement of the fibers, the fibers may be thermally bonded under moisture by using a web containing a hydrophilic fiber (a thermal adhesive fiber under moisture) comprising a thermal adhesive resin under moisture (such as an ethylene-vinyl alcohol copolymer) on at least a surface of the fiber. Specifically, for the steam jet method, when the fiber web transferred by a belt conveyor passes through a high-speed and high-temperature water vapor stream which is jetted or sprayed from a nozzle of a vapor spraying apparatus, the sprayed high temperature water vapor allows the fibers to be entangled with each others. In the presence of the thermal adhesive fibers under moisture, the fibers (the thermal adhesive fibers under moisture or the thermal adhesive fiber under moisture and the hydrophobic fiber) is three-dimensionally bonded to each other by melt-bond of the thermal adhesive fiber under moisture uniformly in the thickness direction.

In order to supply the fiber web with a water vapor, a conventional water vapor spraying apparatus is used. The water vapor spraying apparatus may be attached to each of two belt conveyors for holding the web therebetween in order to spray a high-temperature water vapor from the both sides of the fiber web. As an endless belt used for the conveyor, a net having a mesh count larger than about 90 (for example, a net having a mesh count of about 10 to 60) is usually employed.

In order to spray the high-temperature water vapor, a plate or die having a plurality of predetermined orifices successively arranged in one or a plurality of lines in a width direction thereof is used as a nozzle, and the plate or die is disposed to arrange the orifices in the width direction of the fiber web to be conveyed. The diameter of the orifice is, for example, about 0.05 to 2 mm (particularly about 0.1 to 1 mm). The pitch of the orifice is, for example, about 0.5 to 3 mm (particularly about 1 to 2 mm).

The pressure of the high-temperature water vapor is, for example, about 0.1 to 2 MPa, preferably about 0.2 to 1.5 MPa, and more preferably about 0.3 to 1 MPa. The temperature of the high-temperature water vapor is, for example, about 70 to 150° C., preferably about 80 to 120° C., and more preferably about 90 to 110° C. The speed of the treatment with the high-temperature water is, about not more than 200 m/minute, preferably about 0.1 to 100 m/minute, and more preferably about 1 to 50 m/minute.

[Adhesion Layer]

In contrast to the above-mentioned liquid-retention layer for retaining the liquid component, the adhesion layer, which is directly contacted with the skin, delivers (or moves or transport) a cosmetic preparation from the liquid-retention layer to the skin, and it is necessary for the adhesion layer to have a structure suitable for smooth delivery of the liquid component (e.g., a cosmetic preparation). Thus the adhesion layer is a through-porous structure which allows the liquid component to be delivered from the liquid-retention layer to the skin.

Further, according to the present invention, the adhesion layer (or dense layer) is located at a side directly contacting with the skin, has a soft feel against the skin, closely contacted with the skin by attaching or laying the adhesion layer on the skin, and delivers the liquid component to the skin through pores while retaining the liquid component fed from the liquid-retention layer in the voids between the fibers of the adhesion layer or on the fibers. In particular, according to the present invention, the adhesion layer comprises a nonwoven fabric (or nonwoven structural member) obtained by a melt-blown method or the like, where the fiber of the nonwoven fabric has a uniform and ultrafine fiber diameter. Since such an adhesion layer is a dense layer comprising an ultrafine fiber and has a flat and smooth surface, the contact of the fiber with the skin causes very low scratchy irritation. Further, probably because the adhesion layer is a dense layer comprising the ultrafine fiber, a liquid coat uniformly spreading at the interface between the adhesion layer and the skin is formed. The liquid coat plays an excellent role in a long-time close contact with (or clinging to) the skin.

The nonwoven fabric or nonwoven structural member for the adhesion layer is not particularly limited to specific one as far as the nonwoven fabric or nonwoven structural member is permeable to the liquid component (liquid effective component) while moderately retaining the liquid component. The nonwoven fabric or nonwoven structural member preferably comprises a thermoplastic resin fiber. The thermoplastic resin may include, for example, a polystyrene-series resin, a polyolefin-series resin, an acrylic resin, a poly(vinyl alcohol)-series resin, a poly(vinyl chloride)-series resin, a poly(vinylidene chloride)-series resin, a polyurethane-series resin, a polyester-series resin, a polyether-series resin, a polyamide-series resin, and a thermoplastic elastomer. These thermoplastic resins may be used alone or in combination. Among them, a polyolefin-series resin, a poly(vinyl alcohol)-series resin, a polyester-series resin, a polyurethane-series resin, a thermoplastic elastomer, and others are preferred.

Examples of the polyolefin-series resin may include a polyethylene and a polypropylene. A polypropylene-series resin is low in price, is easily formed into a sheet-shaped nonwoven fabric having a low basis weight, and can stably be produced industrially. In these respects, the polypropylene-series resin (such as a polypropylene) is particularly preferred. In the case where a thin meltblown nonwoven fabric for the adhesion layer is previously produced, rolled up and combined with the liquid-retention layer later by spunlace or other means, use of the polypropylene-series resin for the nonwoven fabric is industrially preferred in the respect that the nonwoven fabric has an excellent releasability and a sufficient strength even in a low basis weight. Further, the fiber diameter of the polypropylene-series resin has a small degree of scattering.

The poly(vinyl alcohol)-series resin may include a poly(vinyl alcohol), an ethylene-vinyl alcohol copolymer, and others. In view of the fiber-forming property, or others, an ethylene-vinyl alcohol copolymer is preferred. As the ethylene-vinyl alcohol copolymer, the ethylene-vinyl alcohol copolymer as exemplified in the liquid-retention layer may be used. The ethylene-vinyl alcohol copolymer is human-friendly due to a low skin irritation and hypoallergenicity. In this respect, the ethylene-vinyl alcohol copolymer is excellent. Further, the ethylene-vinyl alcohol copolymer is highly compatible with both aqueous (water-based) and oily (oil-based) liquid components and can be used for a broad variety of liquid components (e.g., a water-based cosmetic preparation and an oil-based milky lotion).

The polyester-series resin may include, for example, a poly(alkylene arylate) such as a poly(ethylene terephthalate), a poly(trimethylene terephthalate), a poly(butylene terephthalate), or a poly(ethylene naphthalate). Among them, for the same industrial reason as the polypropylene-series resin, a poly($C_{2-4}$alkylene arylate) such as a poly(ethylene terephthalate) or a poly(butylene terephthalate) is preferred. In addition to the production advantage, considering a soft texture and a pleasant feel against the skin, a poly(butylene terephthalate)-series resin such as a poly(butylene terephthalate) is particularly preferred. Further, since the fiber comprising the resin has a high heat resistance in addition to a high fiber strength, the structural change of the fiber due to heating during processing hardly occurs.

Examples of the polyurethane-series resin may include a polyester-based urethane-series resin and a polyether-based urethane-series resin. The polyurethane-series resin can effectively be used, for example, in the case where the following step is adopted: a step of combining the adhesion layer with the liquid-retention layer in the process of the production of the adhesion layer without once rolling up the adhesion layer as a meltblown nonwoven fabric. Further, the polyurethane-series resin imparts a stretchability (or flexibility or elasticity) to a nonwoven fabric (particularly a meltblown nonwoven fabric) made from the resin, and also imparts a stretchability to the resulting laminated sheet. For example, for a facial mask sheet, when the laminated sheet is adhered (or attached) on the skin while applying a tension to any direction, the sheet delivers an effective component to the skin and simultaneously contracts (or shrinks) at the region (or portion) contacted with the skin, thereby stretching the skin. Due to the force, the improvement of wrinkling (or fine lines) and sagging of the skin is also expected. Moreover, when the sheet is applied to a site having a nonuniform thickness (e.g., the arm and the calf) in a wrap-around-like manner, the sheet is hardly slipped off due to the stretchability. In particular, when the sheet is closely contacted with the skin while being stretched, the contractive force produces the feeling that the sheet is attracted to the skin (high adhesion feeling). Among these polyurethane-series resins, in terms of stretchability or the like, a polyester-based urethane-series resin is widely used.

Examples of the thermoplastic elastomer may include an olefinic elastomer, a styrene-series elastomer, a polyester-series elastomer, and a polyamide-series elastomer. For the same reason as the urethane-series resin, these thermoplastic elastomers also have an excellent contractibility and have the same advantages as the polyurethane-series resin.

The fiber for the adhesion layer may also contain the same conventional additives as those described in the liquid-retention layer. Among the additives, for example, addition of a colorant (coloring agent) to the resin as a raw material of the meltblown nonwoven fabric for the adhesion layer allows visually simple discrimination of the adhesion layer (a skin contact surface) in use. Moreover, the impression of commercial products can be managed by selecting the color in consideration of use conditions or user's predilections.

The cross-sectional form of the fiber for the adhesion layer may be the same as that of the fiber for the liquid-retention layer, and is usually a circular form, a elliptical form, and others.

In view of the adhesion to the skin, and others, the diameter of the fiber for the adhesion layer is ultrafine, which is smaller than that of the fiber for the liquid-retention layer. The concrete fiber diameter (number-average fiber diameter) may be not more than 10 µm. For example, the fiber diameter may be about 0.1 to 9 µm, preferably about 0.5 to 8 µm (e.g., about 1 to 8 µm), more preferably 1 to 7 µm (particularly about 1.5 to 6 µm), and particularly preferably about 2 to 6 µm (e.g., about 2 to 5 µm). When the average fiber diameter is excessively small, the adhesion layer deteriorates a function of moving the liquid component (liquid effective component) (such as a cosmetic preparation) from the liquid-retention layer toward the skin. Moreover, when the average fiber diameter is excessively large, the adhesion layer impresses as rough against the skin, and in addition, fails to uniformly spread a liquid coat formed at the interface between the adhesion layer and the skin, whereby deteriorating in the adhesive performance.

The fiber for the adhesion layer is an ultrafine fiber and has a uniform fiber diameter. Specifically, the standard deviation of the fiber diameter may be not more than 5, for example, about 0 to 5, preferably about 0 to 4 (e.g., about 0 to 3), and more preferably about 0 to 2.5 (particularly, about 0 to 2). For example, the standard deviation may be about 0.1 to 5, preferably about 0.5 to 3, and more preferably about 1 to 2. Further, the coefficient of fluctuation of the fiber diameter is about not more than 80%, for example, about 0 to 80%, preferably about 0 to 70%, and more preferably about 0 to 65% (particularly, about 0 to 60%). For example, the coefficient of fluctuation may be about 1 to 80%, preferably about 10 to 70%, and more preferably about 20 to 60%. According to the present invention, since the fiber for the adhesion layer is ultrafine and has a uniform diameter as described above, the fiber causes less irritation to the skin and can form a dense and porous structure.

The basis weight of the nonwoven fabric (or nonwoven structural member) for the adhesion layer is, for example, about 3 to 50 g/m$^2$, preferably about 4 to 30 g/m$^2$, and more preferably about 4 to 20 g/m$^2$ (particularly, about 5 to 10 g/m$^2$). When the basis weight of the nonwoven fabric (particularly, a meltblown nonwoven fabric) is excessively small, the fiber of the liquid-retention layer tends to be exposed on the surface of the adhesion layer. Accordingly, the adhesion layer impresses as rough against the skin, and in addition, fails to uniformly spread a liquid coat formed at the interface between the adhesion layer and the skin, whereby deteriorating in the adhesive performance. When the basis weight of the nonwoven fabric is excessively large, the adhesion layer deteriorates a function of moving the liquid effective component (such as a cosmetic preparation) from the liquid-retention layer toward the skin.

The density of the adhesion layer (the density of the adhesion layer in the laminated sheet) is, for example, about 0.05 to 0.35 g/cm$^3$, preferably about 0.08 to 0.25 g/cm$^3$, and more preferably about 0.1 to 0.2 g/cm$^3$. When the density of the adhesion layer is excessively low, there is not enough amount of the fiber to form the adhesion layer, and it is difficult to form a uniform ultrafine-fiber layer as the adhesion layer. In contrast, when the density of the adhesion layer is excessively high, the adhesion layer deteriorates a function of moving the liquid effective component (such as a cosmetic preparation) from the liquid-retention layer toward the skin.

The void ratio of the adhesion layer (the void ratio of the adhesion layer in the laminated sheet) may be not less than 70% (e.g., about 70 to 99%), preferably not less than 75% (e.g., about 75 to 95%), and more preferably not less than 80% (e.g., about 80 to 90%) in order to uniformly move the liquid effective component (e.g., a cosmetic preparation) fed from the liquid-retention layer toward the skin in a short time.

The thickness of the meltblown nonwoven fabric for the adhesion layer may be selected from the range of about 10 to 500 μm and is, for example, about 30 to 500 μm, preferably about 30 to 200 μm, and more preferably about 35 to 150 μm (particularly, about 40 to 100 μm). When the thickness of the adhesion layer is excessively small, there is not enough amount of the fiber to form the adhesion layer, and it is difficult to form a uniform ultrafine-fiber layer as the adhesion layer. In contrast, when the thickness of the adhesion layer is excessively large, the adhesion layer deteriorates a function of moving the liquid component from the liquid-retention layer toward the skin.

[Process for Producing Adhesion Layer]

The nonwoven fabric or nonwoven structural member for the adhesion layer is not particularly limited to a specific one as far as the process produces a fiber having an ultrafine and uniform diameter for the nonwoven fabric or nonwoven structural member. For the production of the nonwoven fabric or nonwoven structural member, a conventional method can be used. In order to produce a nonwoven fabric comprising a fiber having an ultrafine and uniform diameter, a meltblown method is preferred.

As the meltblown method, there may be used a conventional method, for example, a method which comprises melt-spinning a thermoplastic resin and simultaneously blowing and collecting the resulting fiber by a high-temperature gas. Specifically, a heated and melted resin is extruded (spun) from a nozzle having orifices (spinning holes) arranged in a line; the resin spun from the orifices is attenuated by allowing the resin to contact with a high-temperature air, which is heated to about the same temperature as the nozzle, jetted from slits disposed near the spinning holes; the resulting fiber is laid onto a collector screen which is disposed below the nozzle, forming a sheet-shaped meltblown nonwoven fabric for the adhesion layer. As the production condition of the meltblown method, a conventional condition can be used.

The spinning holes are spaced at, for example, about 100 to 4000 per meter, preferably about 500 to 3000 per meter, and more preferably about 1000 to 2500 per meter. The amount discharged per hole is, for example, about 0.01 to 1 g/hole·min., preferably about 0.05 to 0.5 g/hole·min., and more preferably about 0.1 to 0.3 g/hole·min. The spinning temperature can be selected according to the species of the thermoplastic resin and is, for example, about 150 to 300° C., preferably about 200 to 280° C., and more preferably about 220 to 270° C.

The pressure (air pressure) of the high-temperature air can be selected from the range of about 0.01 to 1 MPa and is, for example, about 0.05 to 0.8 MPa, preferably about 0.1 to 0.6 MPa, and more preferably about 0.2 to 0.5 MPa. The air temperature is preferably, for example, a temperature in the neighborhood of the spinning temperature, e.g., a temperature higher than the spinning temperature by 0 to 50° C., preferably by 3 to 30° C., and more preferably by 5 to 20° C.

The conveyor speed is, for example, about 1 to 200 m/minute, preferably about 5 to 100 m/minute, and more preferably about 10 to 80 m/minute. The air pressure, the conveyor speed, the distance (collecting distance) between the hole (or orifice) of the nozzle and the conveyor (e.g., a net conveyor), and others may suitably be modified so that the basis weight, density, flexibility, and others of the resulting adhesion layer may be adjusted.

[Laminated Sheet]

The laminated sheet of the present invention comprises the liquid-retention layer and the adhesion layer formed on at least one side of the liquid-retention layer. With respect to the thickness ratio of the adhesion layer relative to the liquid-retention layer, according to the present invention, the thickness of the adhesion layer is preferably smaller than that of the liquid-retention layer.

That is, according to the present invention, the adhesion layer is a through-porous structure which allows the liquid component to be delivered from the liquid-retention layer to the skin; and in order to deliver the liquid component (e.g., a cosmetic preparation) smoothly and cover the whole of the skin with a liquid coat of the liquid component (e.g., a cosmetic preparation) uniformly, it is preferable that the liquid-retention layer can be in the vicinity to the skin. In this respect, it is important that the adhesion layer may be thin. The laminated sheet of the present invention achieves a small thickness ratio of the adhesion layer relative to the liquid-retention layer and an extremely small distance between the liquid-retention layer and the skin by using a meltblown nonwoven fabric having a thin porous structure as the adhesion layer, which is located at the side directly contacted with the skin.

Specifically, the thickness ratio of the adhesion layer relative to the liquid-retention layer [the adhesion layer/the liquid-retention layer] is about 1/4 to 1/100, preferably about 1/5 to 1/80, and more preferably about 1/6 to 1/50 (particularly, about 1/7 to 1/30). By increasing the thickness ratio of the liquid-retention layer, the liquid-retention layer can be in the vicinity to the skin, and additionally a larger portion of the laminated sheet has a space suitable for liquid retention as a sheet to be impregnated with the liquid component (e.g., a cosmetic preparation).

The basis weight of the laminated sheet of the present invention is, for example, about 23 to 250 $g/m^2$, preferably about 35 to 150 $g/m^2$, and more preferably about 40 to 120 $g/m^2$.

The laminated sheet of the present invention has an excellent adhesion to the skin. For example, when the laminated sheet is impregnated with a 500% by mass of a cosmetic preparation (skin lotion) (manufactured by Kanebo Cosmetics Inc., "Freshel essence lotion AL") relative to the mass of the sheet and the frictional force (adhesion) of the impregnated sheet is measured in accordance with ASTM-D1984, the frictional force is not less than 0.6 N, for example, about 0.6 to 10 N, preferably about 0.7 to 5 N, and more preferably about 0.8 to 5 N (particularly about 1 to 5 N). Further, when the laminated sheet is impregnated with 900% by mass of the cosmetic preparation, the frictional force is not less than 0.3 N, for example, about 0.3 to 2 N, preferably about 0.4 to 1 N, and more preferably about 0.45 to 0.8 N (particularly about 0.5 to 0.6N). In particular, according to the present invention, the frictional force of the sheet impregnated with 500% by mass of the cosmetic preparation is larger than that of the sheet impregnated with 900% by mass of the cosmetic preparation; and the ratio of the both [the frictional force at 500% by mass impregnation/the frictional force at 900% by mass impregnation] is about 1.1/1 to 10/1, preferably about 1.2/1 to 9/1, and more preferably about 1.3/1 to 8/1 (particularly about 1.5/1 to 7/1). With respect to the impregnation amount of the cosmetic preparation in this test, 900% by mass corresponds to an average initial impregnation ratio in use of a general skin care sheet (for example, a facial mask sheet), and 500% by mass corresponds to an average impregnation ratio in the state where the cosmetic preparation is consumed. Thus, when the laminated sheet of the present invention is used as a skin care sheet (such as a facial mask sheet), the sheet has less peeling-off or slipping-off from the skin due to the improvement of the adhesion followed by the use of the sheet. Incidentally, the frictional force can be measured by a method detailed in Examples described below.

The laminated sheet of the present invention also has an excellent releasability of the retained liquid component. The releasability is tested by applying 30 g of a load to a laminated sheet having a size of 7.5 cm×7.5 cm impregnated with 4.5 g of a cosmetic preparation and measuring an amount of the cosmetic preparation released from the sheet to a filter paper a minute. In this test, the released quantity of the cosmetic preparation is not less than 10% (e.g., about 10 to 50%, and preferably about 20 to 40%). Incidentally, the releasability can be measured by a method detailed in Examples described below.

The laminated sheet of the present invention also has an excellent flexibility under wetting (or in a wet state), and the fibers of the sheet are moderately entangled with each other so that the sheet can be conformed or accorded to the skin (e.g., the face). The sheet has a stress at 50% elongation under wetting in accordance with JIS L 1913, for example, of about 0.5 to 15 N/5 cm, preferably about 1 to 10 N/5 cm, and more preferably about 1 to 5 N/5 cm in at least one direction. A sheet having an excessively small stress at elongation is overstretched when attached to the skin (such as the face), and it is difficult to handle the sheet. A sheet having an excessively large stress at elongation has a lowered adhesion to the skin. Incidentally, the stress at 50% elongation under wetting can be measured by a method detailed in Examples described below.

The laminated sheet of the present invention may further comprise another layer (a third layer) laminated on the liquid-retention layer (a side, on which the adhesion layer is not formed, of the liquid-retention layer).

The third layer can be selected according to the purpose. For example, the user-friendliness of the sheet (e.g., a facial mask sheet) can be improved by forming the above-mentioned adhesion layer on each side of the liquid-retention layer. The thickness of the adhesion layer as the third layer may be the same as that of the adhesion layer described above.

Further, a nonporous film or sheet may be laminated on the liquid-retention layer. When the nonporous film is laminated on the liquid-retention layer and the adhesion layer is contacted with the skin, the liquid component in the liquid-retention layer is sealed and pores in the skin are opened up due to an increase in temperature. Therefore, the absorption of the effective component is easily promoted. The nonporous film or sheet to be used may include a film comprising a thermoplastic resin, for example, a polyolefin sheet, a polyester sheet, a polyamide sheet, and a polyurethane sheet. The thickness of the nonporous film or sheet is, for example, about 3 to 300 μm, preferably about 5 to 100 μm, and more preferably about 5 to 50 μm.

The laminated sheet of the present invention can also be used as an application for absorbing a liquid component, for example, a surface material for a sanitary napkin or a diaper, and a sheet for body fluid absorption (or a skin-washing sheet) such as a diaper liner or a wet wipe (or a pre-moistened wipe). Since the laminated sheet has a well-balanced liquid retentivity and liquid releasability in addition to an excellent adhesion and fit to the skin, it is preferable to be used for an application in which the sheet is impregnated with a liquid component (such as a beauty component or a medicinal component) and closely contacted with the skin. Examples of the application may include various skin care sheets such as a facial mask sheet, a makeup-removing sheet or a cleansing sheet, a body-washing sheet (e.g., a sweat-wiping sheet and an oil-blocking (or oil-absorbing) sheet), a cooling sheet, and a medicated or therapeutic sheet (e.g., an itching-controlling (or antipruritic) sheet and a wet compress).

The skin care sheet of the present invention may be a sheet which is impregnated with these liquid components in use, or a sheet which is previously impregnated with the liquid component (what is called a wet sheet).

According to the present invention, the liquid component may include a liquid substance (such as a solvent or a liquid oil), and in addition, a solution or a dispersion (e.g., a cosmetic preparation and a milky lotion) which contains the effective component (such as a beauty component or a medicinal (efficacious) component) in the liquid substance. The solvent may be a lipophilic solvent. In terms of the safety for the human body, a hydrophilic solvent is preferred. The hydrophilic solvent may include, for example, water, a lower aliphatic alcohol (e.g., a $C_{1-6}$ alkyl alcohol such as ethanol or isopropanol), and an alkylene glycol (e.g., ethylene glycol, diethylene glycol, and propylene glycol). These hydrophilic solvents may be used alone or in combination. The liquid oil may include, for example, an unsaturated higher fatty acid (e.g., oleic acid and oleyl alcohol), an oil derived from animals or plants (e.g., a jojoba oil, an olive oil, a palm oil, a camellia oil, a macadamia nut oil, an avocado oil, a corn oil, a sesame oil, a wheat germ oil, a flaxseed oil, a castor oil, and squalane), a mineral oil (e.g., a liquid paraffin (or petrolatum), a polybutene, and a silicone oil), and a synthetic oil (e.g., a synthetic ester oil and a synthetic polyether oil). These liquid oils may be used alone or in combination.

These liquid substances may be used alone or in combination. For example, the liquid oil may be used as an additive (oil content) in combination with the hydrophilic solvent (such as water or ethanol). Among these liquid substances, usually, water, a lower alcohol or a mixture thereof is employed. Preferably, water and/or ethanol (particularly, water) is used. For example, for the combination use of water with the lower alcohol (particularly, ethanol), the ratio of water relative to the lower alcohol [the water/the lower alcohol] may be about 100/0 to 30/70, preferably about 100/0 to 50/50, more preferably about 100/0 to 70/30, and, e.g., about 99/1 to 80/20.

The effective component (or ingredient) may include a conventional additive, for example, a moisturizing agent, an emollient agent, a cleansing agent, an ultraviolet ray protective agent, a surfactant, an astringent agent, an enzyme, an algefacient, a germicide or an antibacterial agent, a skin-softening agent, an antioxidant, a skin-whitening agent, an antiperspirant, a skin-barrier agent, an anti-inflammatory agent, an agent for controlling skin itching (or an antipruritic), a blood-circulation-promoting agent, an amino acid, a cell-activator, a cooling agent, a perfume, and a coloring agent. These additives may be used alone or in combination. Among these additives, for the skin care sheet, for example, a moisturizing agent, an ultraviolet ray protective agent, a surfactant, an astringent agent, an algefacient, an enzyme, and a germicide or an antibacterial agent, are widely used. In particular, for the facial mask sheet (facial pack) or the cleansing sheet, a moisturizing agent or an emollient agent may be added to a hydrophilic solvent. The moisturizing agent or the emollient agent may include, for example, dipropylene glycol, 1,3-butylene glycol, a polyethylene glycol, a polyoxyethylene-polyoxypropylene block copolymer, a polyoxyethylene sorbitan fatty acid ester, a polyoxyethylene sucrose fatty acid ester, glycerin, sodium hyaluronate, a polyoxymethyl glycoside, a poly(vinyl alcohol), a polyvinylpyrrolidone, and a water-soluble cellulose ether (e.g., a methyl cellulose, a hydroxyethyl cellulose, a hydroxypropyl cellulose, a hydroxyethylmethyl cellulose, and a hydroxypropylmethyl cellulose). The total proportion of the moisturizing agent and the emollient agent is, for example, about 0.1 to 50% by mass, preferably about 1 to 30% by mass, and more preferably about 5 to 20% by mass in the solution.

The proportions of these additives may suitably be selected according to the purposes. For example, the proportion of the liquid substance (such as water or ethanol) is usually about 30 to 99% by mass, preferably about 40 to 95% by mass, and more preferably about 50 to 90% by mass in the total liquid component containing the additive(s).

Since the laminated sheet of the present invention has an excellent adhesion to the skin, the laminated sheet is particularly suitable for a sheet to be fixed on the skin (such as a facial mask sheet or a wet compress). For example, due to a strong adhesion, no slipping-off or peeling-off of the sheet occurs even when used for a long time, and the sheet can be conformed to the fine (or small) curvature or gap of the skin (e.g., the root of the nose) without leaving space. Thus, the effective component of the facial mask sheet can effectively infiltrate in the skin.

The laminated sheet of the present invention is also suitable for a cleansing sheet or a skin-washing sheet, and the like. Specifically, since the laminated sheet of the present invention has a large contact area to the skin and strongly adheres to the skin, the sheet can be conformed to the fine (or small) curvature or gap of the face without leaving space. Therefore, the sheet can effectively remove a makeup (e.g., a makeup cosmetic preparation such as a foundation, a face powder, a lipstick, or an eye makeup) from the skin. Further, since the adhesion layer is formed from a uniform and ultrafine fiber, the sheet has extremely less irritation to the skin and can also effectively remove dirt from pores in the skin.

Thus, when the laminated sheet of the present invention is used as a living-body application sheet for liquid impregnation (e.g., a facial mask sheet and a cleansing sheet), usually the laminated sheet is impregnated with the liquid component and then applied to or contacted with the skin of a living body.

[Process for Producing Laminated Sheet]

The process for producing the laminated sheet of the present invention is not particularly limited to a specific one as far as the liquid-retention layer and the adhesion layer are integrated (or combined). For example, the liquid-retention layer and the adhesion layer, each separately obtained by the above-mentioned production process, may be integrated by adhesion, entangling, and other means. As the entangling method, the spunlace method, the needle punch method, the steam jet method, and others, which are exemplified in the paragraph of the liquid-retention layer, may be used. As the method for adhering the liquid-retention layer to the adhesion layer, a method of directly blowing a fiber for the adhesion layer to the resulting liquid-retention layer (direct blown method), and other methods can be used. Among them, in terms of convenience and others, the spunlace method is widely used.

Further, with respect to the production process of the laminated sheet of the present invention, for example, the liquid-retention layer and the adhesion layer may be produced continuously, the liquid-retention layer and the adhesion layer may be integrated with each other by connecting the respective production lines for nonwoven fabric to each other, and one of these layers may be produced and then introduced or incorporated in the production process for the other layer to integrate these layers. For example, from industrial point of view, the following methods may be used: a method which comprises introducing or incorporating a meltblown nonwoven fabric for the adhesion layer in a production line for spunlace nonwoven fabric, and entangling both fibers by a water flow in a spunlace method or others to integrate these layers; a method which comprises introducing or incorporating a nonwoven fabric for the liquid-retention layer in a production line for a meltblown nonwoven fabric for the adhesion layer, and collecting melt-blown fibers onto the nonwoven fabric for the liquid-retention layer as a collector screen to integrate these layers (direct blown method); and others.

EXAMPLES

Hereinafter, the following examples are intended to describe this invention in further detail and should by no means be interpreted as defining the scope of the invention. Incidentally, each of physical properties in Examples and Comparative Examples was determined or evaluated as follows.

[Basis Weight $(g/m^2)$]

In accordance with JIS L 1906, a sample was allowed to stand for 24 hours in a standard state (a temperature of 20° C. and a humidity of 65%) and then a specimen having a width of 1 m and a length of 1 m was obtained from the sample, and the weight (g) of the specimen was scaled. The measured value (g) was rounded off to the closest whole number, and the calculated value was taken as a basis weight.

[Thickness (μm)]

A sample was cut along (or parallel to) an MD direction in a direction perpendicular to a sample surface thereof with a razor (manufactured by FEATHER Safety Razor Co., Ltd., "Feather Razor S, single-edged"). The cut surface (or cross-sectional surface) of the specimen was observed with a digital microscope [manufactured by KEYENCE Corporation, DIGITAL MICROSCOPE VHX-900] and the thickness of the specimen was measured.

[Density $(g/cm^3)$]

The basis weight $(g/m^2)$ was divided by the thickness to determine the density.

[Void Ratio (%)]

The void ratio was calculated using the following equation based on the weight (g) of the nonwoven fabric, the specific gravity of the fiber $(g/cm^3)$, the apparent volume of the nonwoven fabric $(cm^3)$. Incidentally, the apparent volume of the nonwoven fabric was calculated by multiplication of the area of the sheet surface of the nonwoven fabric and the value (as height) obtained through the measurement of the thickness.

$$\text{Void ratio (\%)}=100-[(\text{weight}\times 100)/(\text{specific gravity of fiber}\times\text{apparent volume of nonwoven fabric})]$$

[Average Fiber Diameter (μm)]

A fiber sheet was cut into a test piece (length×width=5 cm×5 cm), and a micrograph of the central region (a region with center at the intersection of the diagonals) of the surface of the test piece was taken using a scanning electron microscope (SEM) with 1000 magnifications. A circle with radius 30 cm and center at the central region (the intersection of the diagonals) of the obtained micrograph was drawn on the micrograph, and 100 fibers were randomly selected from the inside of the circle. Each fiber diameter at the central region or a neighborhood thereof in the length direction was measured with vernier calipers, and the average value was taken as an average fiber diameter (number-average fiber diameter). Incidentally, the fiber diameters of all fibers shown in the micrograph were determined without distinction between a fiber located on the surface of the fiber sheet and a fiber located in the inside of the fiber sheet.

[Distribution of Fiber Diameter]

The nonwoven structure of the adhesion layer was observed using a scanning electron microscope. One hundred (100) fibers (50 fibers in Examples 3 and 4 and Comparative Example 5) were randomly selected on an electron micrograph, and each fiber diameter was measured to determine the number-average fiber diameter and the standard deviation. Further, the coefficient of fluctuation of the fiber diameter was calculated based on the following equation.

Coefficient of fluctuation (%)=Standard deviation/ Number-average fiber diameter×100

[Adhesion]

Figure 2:
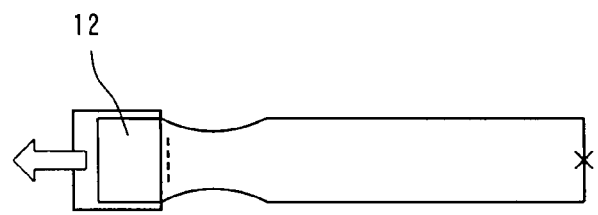
FIG. 2 is a schematic plan view illustrating an outline of a test method of a sample for an adhesion test.
Figure 3:
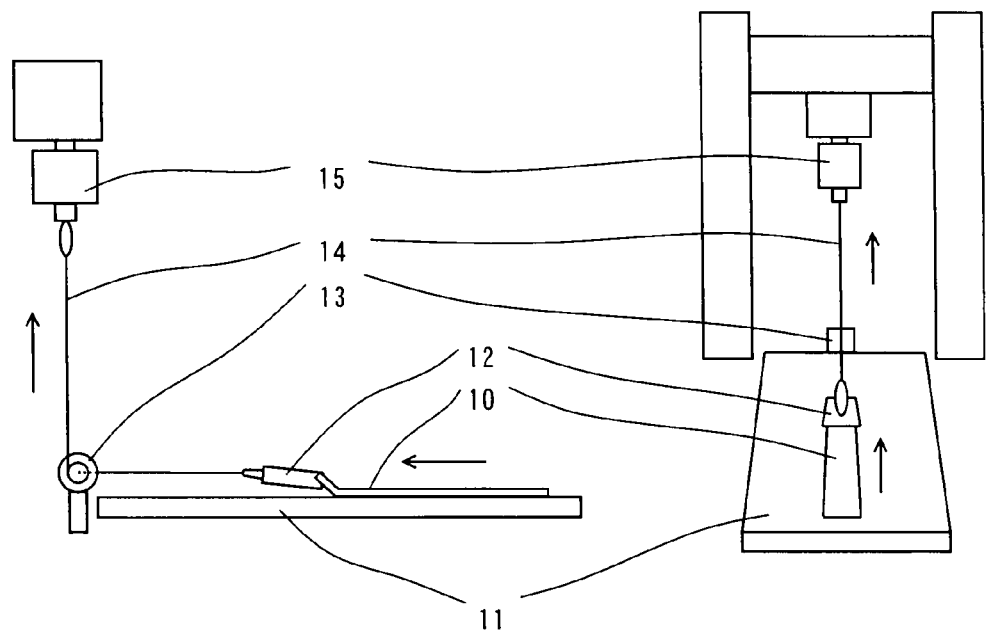
FIG. 3 is a schematic side view and a schematic perspective view (a perspective view observed from the front direction) of a test apparatus for an adhesion test.
Figure 4:
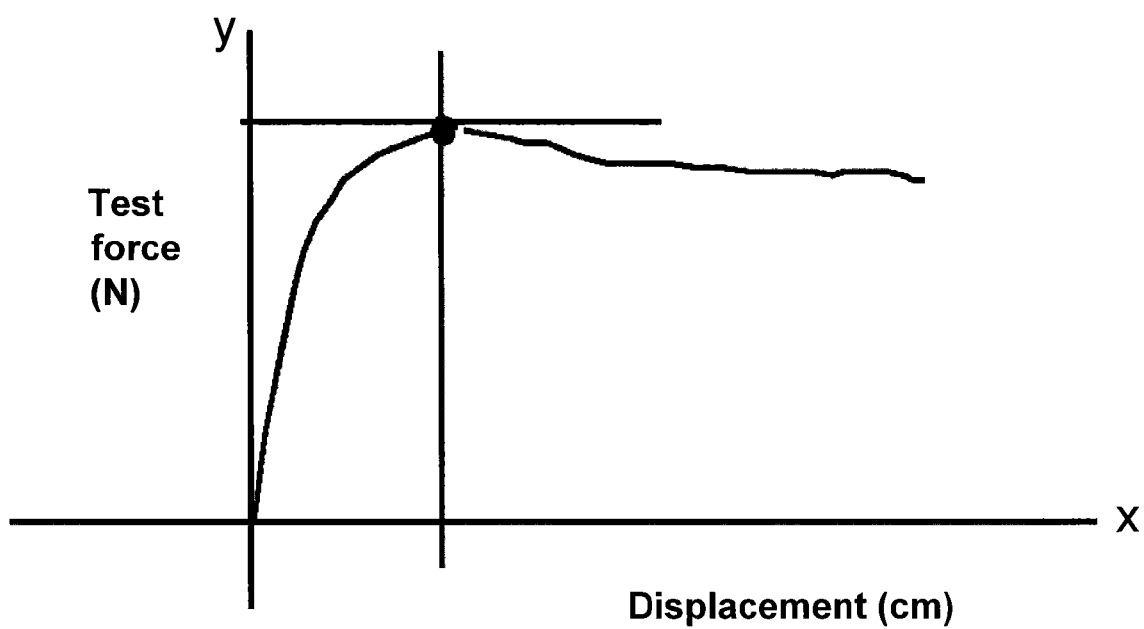
FIG. 4 is a graph representing a relationship between a test force and a displacement of a sample in an adhesion test.

Using a precision universal tester (manufactured by Shimadzu Corporation, "Autograph AGS-D type"), the frictional force was measured in accordance with ASTM-D1894. As shown in FIG. 1, a sample 10 which was cut to 4.0 cm in MD direction and 11.0 cm in CD direction had a gripped portion 10a having a length of 1 cm in CD direction, and a ground portion 10b having a length of 10 cm in CD direction. Further, on the assumption that the sample was used as a facial mask sheet, the sample was impregnated with a cosmetic preparation (manufactured by Kanebo Cosmetics Inc., "Freshel essence lotion AL") in a proportion of the following two different percents by mass. As shown in FIG. 2, for a test, the gripped portion 10a of the sample 10 was held by a clip 12 and pulled toward the direction of the arrow. Specifically, as shown in FIG. 3, an acrylic board was fixed on a table 11 for measuring a frictional force, and the sample was placed on the center of the acrylic board so that the skin contact side thereof might be down side. Further, a load of 10 g/cm$^2$ was applied to the area of 4.0 cm in MD direction and 10.0 cm in CD direction (the ground portion 3) of the sample for 10 seconds using a tester equipped with a load cell 15, and then the sample was horizontally pulled in CD direction with a speed of 20 mm/min. by pulling a polyamide yarn 14 horizontally through a pulley 13, and the peak value of the resulting test force (the peak value shown in FIG. 4) was defined as the adhesion. Incidentally, the adhesion was measured in the following two conditions.

(1) The sample was impregnated with 900% by mass of the cosmetic preparation relative to the mass of the sample, and the value of the adhesion was obtained under the condition modeled on the environment immediately after the face mask sheet was used.

(2) The sample was impregnated with 500% by mass of the cosmetic preparation relative to the mass of the sample, and the value of the adhesion was obtained under the condition modeled on the environment in the latter half of the use of the face mask sheet.

Incidentally, the cosmetic preparation is an aqueous cosmetic preparation containing water and a hydrophilic material as main components, and is a composition containing water, glycerin, ethanol, dipropylene glycol, multitol, PEG-75, raffinose, phenyl trimethicone, Carbomer K, Polysorbate 20, perfluoroalkyl dimethicone polyol, 1,3-butylene glycol, cucumber extract, PEG-60 hydrogenated castor oil, xanthan gum, aloe vera (aloe barbadensis leaf) extract-1, edetate, phenoxyethanol, and paraben.

[Adhesion Feeling]

A sample which was cut into a shape of a facial mask was impregnated with 900% by mass of a cosmetic preparation (manufactured by Kanebo Cosmetics Inc., "Freshel essence lotion AL") relative to the mass of the sample, and the sample was used as a facial mask sheet in a straighten up position. As a sensory test, the adhesion feeling after using the sample for 20 minutes was evaluated by five (5) subjects on the basis of the following criteria.

<Evaluation Criteria>

"A": The sample had a good conformity to the skin, and the adhesion feeling was unchanged or improved compared with the adhesion feeling immediately after using the sample.

"B": Although the sample had a good conformity to the skin, the adhesion feeling was lowered compared with the adhesion feeling immediately after using the sample.

"C": The sample had a bad conformity to the skin, and slipping-off or peeling-off occurred. Moreover, the adhesion feeling was significantly lowered compared with the adhesion feeling immediately after using the sample.

[Cosmetic Preparation Releasability]

A sample which was cut to a size of 7.5 cm×7.5 cm was placed on a metal plate treated with Teflon (registered trademark) so that the skin contact surface thereof might be down side.

Nine hundred percent (900%) by mass of a cosmetic preparation (manufactured by Kanebo Cosmetics Inc., "Freshel essence lotion AL") relative to the mass of the sample was weighed (the cosmetic preparation weight C), and the whole quantity of the cosmetic preparation was added dropwise to the sample from the opposite side of the skin contact side of the sample (from the liquid-retention layer side). The cosmetic preparation was spread by a spatula so that the sample was almost uniformly impregnated with the cosmetic preparation. A filter paper (ADVANTEC FILTER PAPER GLADE 2) was cut to a size of 10.0 cm×10.0 cm, and five sheets of the filter paper were put in layers and weighed (filter paper weight A). Using the filter paper in place of the skin, the sample impregnated with the cosmetic preparation was placed on the filter paper, and 30 g of an acrylic board as a load was placed on the specimen so that the whole surface of the specimen might be covered with the acrylic board. After leaving for one minute, the specimen and the load were removed, and the filter paper was weighed (filter paper weight B). The cosmetic preparation releasability was determined from the weight of the cosmetic preparation moved from the specimen to the filter paper according to the following equation.

Cosmetic preparation releasability (%)=(Filter paper weight $B$−Filter paper weight $A$)÷Cosmetic preparation weight $C$×100

[Stress at 50% Elongation Under Wetting]

In accordance with a method described in JIS L 1913 (Nonwoven fabric made of staple fibers) 6.3.2 (Tensile strength and elongation percentage tests under wetting), the stress at 50% elongation under wetting was measured. Specifically, the sample was put in water at 20° C.±2° C. and then the sample was left until the sample sank under gravitation, or the sample was submerged in water for not less than one hour; and thereafter the sample was taken out of the water, and immediately the stress at 50% elongation was measured.

As raw materials for a laminated sheet, the following materials were provided.

[Rayon fiber]: a regenerated cellulose fiber, manufactured by OmiKenshi Co., Ltd., "HOPE", average fiber diameter of 12 μm, fiber length of 40 mm

[Tencel fiber]: a purified cellulose fiber, manufactured by Lenzing, "LYOCELL", average fiber diameter of 12 μm, fiber length of 38 mm

[Polyester fiber]: a poly(ethylene terephthalate) (PET) fiber, manufactured by Toray Industries, Inc., average fiber diameter or 12 μm, fiber length or 51 mm

[Split fiber]: a split fiber in which the cross section has a layer structure containing a polyamide layer and a polyester layer, manufactured by Kuraray Co., Ltd., "WRAMP", average fiber diameter of 17 µm, fiber length if 51 mm (average fiber diameter of 5 µm after splitting)

[Cotton fiber]: a cotton fiber, manufactured by Marusan Industry Co., Ltd., average fiber diameter of 14 µm

[Sheath-core conjugated fiber]: a sheath-core conjugated fiber comprising a poly(ethylene terephthalate) as a core and an ethylene-vinyl alcohol copolymer (EVOH) as a sheath, manufactured by Kuraray Co., Ltd., "SOPHISTA", average fiber diameter of 14 µm, fiber length of 51 mm

[Polypropylene (PP) resin]: MFR (230° C., 2.16 kg)=1100 g/10 minutes

[Ethylene-vinyl alcohol copolymer resin (EVOH)]: MFR (190° C., 2.16 kg)=12 g/10 minutes

[Poly(butylene terephthalate) (PBT) resin]: MFR (235° C., 2.16 kg)=90 g

[Polyurethane resin]: melt viscosity of $1.0 \times 10^3$ to $5.0 \times 10^3$ Pa·s/200° C. by D-65935 fixed temperature method

[Polyester film]: a poly(ethylene terephthalate) film, manufactured by Toray Industries, Inc., "LUMIRROR PX52", basis weight of 16.6 g/m$^2$, thickness of 12 µm

[Adhesive resin]: LD polyethylene, manufactured by Tosoh Corporation, "Nipolon"

Example 1

Using a general meltblown production equipment, 100 parts by mass of the polypropylene resin (MFR=1100 g/10 minutes) was spun by a meltblown method at a spinning temperature of 260° C., an air temperature of 270° C., an air pressure of 0.4 MPa, a discharged amount of 0.2 g/hole·min., the number of spinning holes in mouthpiece of 400 (arranged in a line), and the resulting fiber was collected on a rotating net conveyor as a support to produce a meltblown nonwoven fabric sheet having a basis weight of 5 g/m$^2$, and the sheet was rolled up.

Forty (40) parts by mass of the rayon fiber and 60 parts by mass of the polyester fiber were blended uniformly, and then a semi-random card web having a basis weight of 60 g/m$^2$ was produced in the usual manner. The card web was placed on a punching drum support having an open area ratio of 25% and a hole diameter of 0.3 mm. The card web was continuously moved at a speed of 50 m/minute in a longitudinal direction thereof, and simultaneously subjected to a high-pressure water flow jet from above for entangling treatment to give an entangled fiber web (nonwoven fabric). In the entangling treatment, two nozzles (first and second nozzles) were used; where each nozzle had orifices arranged at an interval of 0.6 mm along the width direction (cross direction) of the web, each orifice had a hole diameter of 0.10 mm, and the distance between these nozzles were 20 cm. The water pressure of the high-pressure water flow jetted from the first nozzle (upstream side) was 3.0 MPa, and that from the second nozzle (downstream side) was 4.0 MPa. The previously produced meltblown nonwoven fabric sheet having a basis weight of 5 g/m$^2$ was unwound with a unwinding apparatus, and superposed on the web. The sheet and the web were placed on an entirely flat support having a finer mesh, and continuously moved, and simultaneously subjected to a high-pressure water flow jet for entangling treatment to entangle fibers constituting the two nonwoven fabrics and give combine these fabrics with each other. The entangling treatment was carried out using two nozzles, where each nozzle had orifices arranged at an interval of 0.6 mm along the width direction (cross direction) of the web, and each orifice had a hole diameter of 0.10 mm; and the water pressure of the high-pressure water flow from each nozzle was 5 MPa. Further, the resulting member was dried at 120° C. to give a combined nonwoven fabric having a basis weight of 65 g/m$^2$.

With respect to the resulting nonwoven fabric sheet, the thickness ratio was 10.6 of the liquid-retention layer relative to one (1) of the adhesion layer. Moreover, the fiber of the adhesion layer composed of the meltblown nonwoven fabric in the resulting nonwoven fabric sheet had a number-average fiber diameter of 2.57 µm and a standard deviation of fiber diameter distribution of 1.318, and the coefficient of fluctuation of the fiber diameter was 51.26%. Furthermore, in the resulting nonwoven fabric sheet, the liquid-retention layer had a void ratio of 90.4%, and the adhesion layer had a void ratio of 86.6%.

The sheet was impregnated with the cosmetic preparation, and the adhesion of the sheet was measured. The adhesion of the sheet impregnated with 900% by mass of the cosmetic preparation, which was an average initial impregnation rate of a typical facial mask sheet, was compared with the adhesion of the sheet impregnated with 500% by mass of the cosmetic preparation, which was modeled on the impregnation ratio in the state that the cosmetic preparation was consumed; and the adhesion of the sheet having an impregnation rate of 500% by mass was higher than that having an impregnation rate of 900% by mass. It was concluded from the results that the adhesion of the sheet was increased after use.

The adhesion feeling was evaluated by the sensory test, and all of five subjects judged the adhesion feeling to be "A". It was concluded from the results that the adhesion feeling is good in use. The cosmetic preparation releasability was not less than 10%. It was concluded from the results that the sheet had a good function to release the cosmetic preparation toward the skin in use.

Example 2

In the same manner as in Example 1 except that the basis weight of the semi-random card web was 40 g/m$^2$, a combined nonwoven fabric having a basis weigh of 45 g/m$^2$ was obtained. With respect to the resulting nonwoven fabric sheet, the thickness ratio was 8.7 of the liquid-retention layer relative to one (1) of the adhesion layer. Moreover, the fiber of the adhesion layer composed of the meltblown nonwoven fabric in the resulting nonwoven fabric sheet had a number-average fiber diameter of 2.57 µm and a standard deviation of fiber diameter distribution of 1.318, and the coefficient of fluctuation of the fiber diameter was 51.26%. Furthermore, in the resulting nonwoven fabric sheet, the liquid-retention layer had a void ratio of 93.3%, and the adhesion layer had a void ratio of 88.6%.

The sheet was impregnated with the cosmetic preparation, and the adhesion of the sheet was measured. As with Example 1, the adhesion of the sheet having an impregnation rate of 500% by mass was higher than that having an impregnation rate of 900% by mass. It was concluded from the results that the adhesion of the sheet was increased after use.

The adhesion feeling was evaluated by the sensory test, and all of five subjects judged the adhesion feeling to be "A". It was concluded from the results that the adhesion feeling is good in use. The cosmetic preparation releasability was not less than 10%. It was concluded from the results that the sheet had a good function to release the cosmetic preparation toward the skin in use.

Example 3

Using a general meltblown production equipment, 100 parts by mass of the poly(butylene terephthalate) resin (MFR=90 g/10 minutes) was spun by a meltblown method at a spinning temperature of 280° C., an air temperature of 290° C., an air pressure of 0.4 MPa, a discharged amount of 0.3/hole·min., the number of spinning holes in mouthpiece of 400 (arranged in a line), and the resulting fiber was collected on a rotating net conveyor as a support to produce a meltblown nonwoven fabric sheet having a basis weight of 20 g/m$^2$, and the sheet was rolled up.

In the same manner as in Example 1, an entangled fiber web (nonwoven fabric) was produced using 40 parts by mass of the rayon fiber and 60 parts by mass of the polyester fiber. The previously produced meltblown nonwoven fabric sheet having a basis weight of 20 g/m$^2$ was unwound with a unwinding apparatus, and superposed on the web. The sheet and the web were placed on an entirely flat support having a finer mesh, and continuously moved, and simultaneously subjected to a high-pressure water flow jet for entangling treatment to entangle fibers constituting the two nonwoven fabrics and give combine these fabrics with each other. The entangling treatment was carried out using two nozzles, where each nozzle had orifices arranged at an interval of 0.6 mm along the width direction (cross direction) of the web, and each orifice had a hole diameter of 0.10 mm; and the water pressure of the high-pressure water flow from each nozzle was 5 MPa. Further, the resulting member was dried at 130° C. to give a combined nonwoven fabric having a basis weight of 80 g/m$^2$.

With respect to the resulting nonwoven fabric sheet, the thickness ratio was 5.7 of the liquid-retention layer relative to one (1) of the adhesion layer. Moreover, the fiber of the adhesion layer composed of the meltblown nonwoven fabric in the resulting nonwoven fabric sheet had a number-average fiber diameter of 5.26 µm and a standard deviation of fiber diameter distribution of 1.504, and the coefficient of fluctuation of the fiber diameter was 28.59%. Furthermore, in the resulting nonwoven fabric sheet, the liquid-retention layer had a void ratio of 90.9%, and the adhesion layer had a void ratio of 81.2%.

The sheet was impregnated with the cosmetic preparation, and the adhesion of the sheet was measured. As with Example 1, the adhesion of the sheet having an impregnation rate of 500% by mass was higher than that having an impregnation rate of 900% by mass. It was concluded from the results that the adhesion of the sheet was increased after use.

The adhesion feeling was evaluated by the sensory test, and all of five subjects judged the adhesion feeling to be "A". It was concluded from the results that the adhesion feeling is good in use. The cosmetic preparation releasability was not less than 10%. It was concluded from the results that the sheet had a good function to release the cosmetic preparation toward the skin in use.

Example 4

Using a general meltblown production equipment, 100 parts by mass of the ethylene-vinyl alcohol copolymer resin (MFR (190° C., 2.16 kg)=12 g/10 minutes) was spun by a meltblown method at a spinning temperature of 250° C., an air temperature of 260° C., an air pressure of 0.4 MPa, a discharged amount of 0.2 g/hole·min., the number of spinning holes in mouthpiece of 400 (arranged in a line), and the resulting fiber was collected on a rotating net conveyor as a support to produce a meltblown nonwoven fabric sheet having a basis weight of 20 g/m$^2$.

Forty (40) parts by mass of the Tencel fiber and 60 parts by mass of the sheath-core conjugated fiber were blended uniformly, and then a semi-random card web having a basis weight of 80 g/m$^2$ was produced in the usual manner. In the same manner as in Example 1, a fiber web (nonwoven fabric) was produced. The previously produced meltblown nonwoven fabric sheet having a basis weight of 20 g/m$^2$ was unwound with a unwinding apparatus, and superposed on the web. The sheet and the web were placed on an entirely flat support having a finer mesh, and continuously moved, and simultaneously subjected to a high-pressure water flow jet for entangling treatment to entangle fibers constituting the two nonwoven fabrics and give combine these fabrics with each other. The entangling treatment was carried out using two nozzles, where each nozzle had orifices arranged at an interval of 0.6 mm along the width direction (cross direction) of the web, and each orifice had a hole diameter of 0.10 mm; and the water pressure of the high-pressure water flow from each nozzle was 5 MPa. Further, the resulting member was dried at 110° C. to give a combined nonwoven fabric having a basis weight of 100 g/m$^2$.

With respect to the resulting nonwoven fabric sheet, the thickness ratio was 5.2 of the liquid-retention layer relative to one (1) of the adhesion layer. Moreover, the fiber of the adhesion layer composed of the meltblown nonwoven fabric in the resulting nonwoven fabric sheet had a number-average fiber diameter of 6.73 µm and a standard deviation of fiber diameter distribution of 2.813, and the coefficient of fluctuation of the fiber diameter was 41.81%. Furthermore, in the resulting nonwoven fabric sheet, the liquid-retention layer had a void ratio of 90.0%, and the adhesion layer had a void ratio of 85.1%.

The sheet was impregnated with the cosmetic preparation, and the adhesion of the sheet was measured. As with Example 1, the adhesion of the sheet having an impregnation rate of 500% by mass was higher than that having an impregnation rate of 900% by mass. It was concluded from the results that the adhesion of the sheet was increased after use.

The adhesion feeling was evaluated by the sensory test, and all of five subjects judged the adhesion feeling to be "A". It was concluded from the results that the adhesion feeling is good in use. The cosmetic preparation releasability was not less than 10%. It was concluded from the results that the sheet had a good function to release the cosmetic preparation toward the skin in use.

Example 5

Forty (40) parts by mass of the rayon fiber and 60 parts by mass of the polyester fiber were blended uniformly, and then a semi-random card web having a basis weight of 60 g/m$^2$ was produced in the usual manner. The card web was placed on a punching drum support having an open area ratio of 25% and a hole diameter of 0.3 mm. The card web was continuously moved at a speed of 50 m/minute in a longitudinal direction thereof, and simultaneously subjected to a high-pressure water flow jet from above for entangling treatment to give an entangled fiber web (nonwoven fabric). In the entangling treatment, two nozzles (first and second nozzles) were used; where each nozzle had orifices arranged at an interval of 0.6 mm along the width direction (cross direction) of the web, each orifice had a hole diameter of 0.10 mm, and the distance between these nozzles were 20 cm. The water pressure of the high-pressure water flow jetted from the first nozzle was 3.0 MPa, and that from the second nozzle was 4.0 MPa. The web was placed on an entirely flat support having a finer mesh, and continuously moved, and simultaneously subjected to a high-pressure water flow jet for entangling treatment to entangle fibers constituting the web. The entangling treatment was carried out using two nozzles, where each nozzle had orifices arranged at an interval of 0.6 mm along the width direction (cross direction) of the web, and each orifice had a hole diameter of 0.10 mm; and the water pressure of the high-pressure water flow from each nozzle was 5 MPa. Further, the resulting member was dried at 110° C. to give a spunlace nonwoven fabric having a basis weight of 60 g/m².

Using a general meltblown production equipment, 100 parts by mass of the urethane resin (melt viscosity of $1.0 \times 10^3$ to $5.0 \times 10^3$ Pa·s/200° C. by D-65935 fixed temperature method) was spun by a meltblown method at a spinning temperature of 250° C., an air temperature of 260° C., an air pressure of 0.4 MPa, a discharged amount of 0.2 g/hole·min., the number of spinning holes in mouthpiece of 400 (arranged in a line). The previously produced spunlace nonwoven fabric was placed on a rotating net conveyor as a support, and the resulting spun fiber was collected thereon to give a combined nonwoven fabric having a basis weight of 65 g/m².

With respect to the resulting nonwoven fabric sheet, the thickness ratio was 14.2 of the liquid-retention layer relative to one (1) of the adhesion layer. Moreover, the fiber of the adhesion layer composed of the meltblown nonwoven fabric in the resulting nonwoven fabric sheet had a number-average fiber diameter of 3.75 μm and a standard deviation of fiber diameter distribution of 2.253, and the coefficient of fluctuation of the fiber diameter was 60.08%. Furthermore, in the resulting nonwoven fabric sheet, the liquid-retention layer had a void ratio of 90.5%, and the adhesion layer had a void ratio of 86.0%.

The sheet was impregnated with the cosmetic preparation, and the adhesion of the sheet was measured. As with Example 1, the adhesion of the sheet having an impregnation rate of 500% by mass was higher than that having an impregnation rate of 900% by mass. It was concluded from the results that the adhesion of the sheet was increased after use.

The adhesion feeling was evaluated by the sensory test, and all of five subjects judged the adhesion feeling to be "A". It was concluded from the results that the adhesion feeling is good in use. The cosmetic preparation releasability was not less than 10%. It was concluded from the results that the sheet had a good function to release the cosmetic preparation toward the skin in use.

Example 6

Thirty (30) parts by mass of the sheath-core conjugated fiber and 70 parts by mass of the polyester fiber were blended uniformly, and then a semi-random card web having a basis weight of 100 g/m² was produced in the usual manner. The card web was transferred to a belt conveyor equipped with a 50-mesh stainless-steel endless net having a width of 500 mm. Incidentally, above the belt conveyor, a belt conveyor having the same metal mesh was disposed, the belt conveyors independently revolved at the same speed rate in the same direction, and the clearance between the metal meshes was adjustable arbitrarily. Then the card web was introduced to a water vapor spraying apparatus attached on the lower belt conveyor. The card web was subjected to a water vapor treatment by spraying the card web (perpendicularly) with a high-temperature water vapor jetted at a pressure of 0.4 MPa from the water vapor spraying apparatus so that the water vapor penetrated the web in the thickness direction of the web to give a shaped product having a nonwoven structure (steam-jet nonwoven fabric). The water vapor spraying apparatus had a nozzle disposed in the inside of the under conveyor so as to spray to the web with the high-temperature water vapor through the conveyor net. A suction apparatus was disposed inside the upper conveyor. In a downstream side in the web traveling direction with respect to this spraying apparatus, another pair of a nozzle and a suction apparatus in inverse arrangement of the above pair was disposed. In this way, the both surfaces of the web were subjected to the water vapor treatment. Incidentally, the water vapor spraying apparatus used had nozzles, each having a pore size of 0.3 mm, and these nozzles were arranged in a line parallel to the width direction of the conveyor in a pitch of 1 mm. The processing speed was 10 m/minute, and the clearance (distance) between the upper and lower conveyor belts was 5 mm. Each of the nozzles was disposed on the backside of the belt so that the nozzle almost contacted with the belt.

Using the urethane resin, a meltblown spinning was carried out in the same manner as in Example 5. The previously produced steam-jet nonwoven fabric was placed on a rotating net conveyor as a support, and the resulting spun fiber was collected thereon to give a combined nonwoven fabric having a basis weight of 110 g/m².

With respect to the resulting nonwoven fabric sheet, the thickness ratio was 26.9 of the liquid-retention layer relative to one (1) of the adhesion layer. Moreover, the fiber of the adhesion layer composed of the meltblown nonwoven fabric in the resulting nonwoven fabric sheet had a number-average fiber diameter of 3.89 μm and a standard deviation of fiber diameter distribution of 2.482, and the coefficient of fluctuation of the fiber diameter was 63.79%. Furthermore, in the resulting nonwoven fabric sheet, the liquid-retention layer had a void ratio of 93.5%, and the adhesion layer had a void ratio of 79.3%.

The sheet was impregnated with the cosmetic preparation, and the adhesion of the sheet was measured. As with Example 1, the adhesion of the sheet having an impregnation rate of 500% by mass was higher than that having an impregnation rate of 900% by mass. It was concluded from the results that the adhesion of the sheet was improved after use. The adhesion feeling was evaluated by the sensory test, and all of five subjects judged the adhesion feeling to be "A". It was concluded from the results that the adhesion feeling is good in use. The cosmetic preparation releasability was not less than 10%. It was concluded from the results that the sheet had a good function to release the cosmetic preparation toward the skin in use.

Example 7

In the same manner as in Example 1, the polypropylene resin was used to produce a meltblown nonwoven fabric sheet having a basis weight of 5 g/m².

Twenty (20) parts by mass of the rayon fiber and 80 parts by mass of the polyester fiber were blended uniformly, and then a semi-random card web having a basis weight of 95 g/m² was produced in the usual manner. In the same manner as in Example 1, an entangled fiber web (nonwoven fabric) was produced. In the entangling treatment, two nozzles (first and second nozzles) were used; where each nozzle had orifices arranged at an interval of 0.6 mm along the width direction (cross direction) of the web, each orifice had a hole diameter of 0.10 mm, and the distance between these nozzles were 20 cm. The water pressure of the high-pressure water flow jetted from the first nozzle was 5.0 MPa, and that from the second nozzle was 6.0 MPa. The previously produced meltblown nonwoven fabric sheet having a basis weight of 5 g/m² was unwound with a unwinding apparatus, and superposed on the web. The sheet and the web were placed on an entirely flat support having a finer mesh, and continuously moved, and simultaneously subjected to a high-pressure water flow jet for entangling treatment to entangle fibers constituting the two nonwoven fabrics and give combine these fabrics with each other. The entangling treatment was carried out using two nozzles, where each nozzle had orifices arranged at an interval of 0.6 mm along the width direction (cross direction) of the web, and each orifice had a hole diameter of 0.10 mm; and the water pressure of the high-pressure water flow from each nozzle was 5 MPa. Further, the resulting member was dried at 120° C. to give a combined nonwoven fabric having a basis weight of 100 g/m².

With respect to the resulting nonwoven fabric sheet, the thickness ratio was 20.3 of the liquid-retention layer relative to one (1) of the adhesion layer. Moreover, the fiber of the adhesion layer composed of the meltblown nonwoven fabric in the resulting nonwoven fabric sheet had a number-average fiber diameter of 2.57 μm and a standard deviation of fiber diameter distribution of 1.318, and the coefficient of fluctuation of the fiber diameter was 51.26%. Furthermore, in the resulting nonwoven fabric sheet, the liquid-retention layer had a void ratio of 92.8%, and the adhesion layer had a void ratio of 88.1%.

The sheet was impregnated with the cosmetic preparation, and the adhesion of the sheet was measured. As with Example 1, the adhesion of the sheet having an impregnation rate of 500% by mass was higher than that having an impregnation rate of 900% by mass. It was concluded from the results that the adhesion of the sheet was increased after use.

The adhesion feeling was evaluated by the sensory test, and all of five subjects judged the adhesion feeling to be "A". It was concluded from the results that the adhesion feeling is good in use. The cosmetic preparation releasability was not less than 10%. It was concluded from the results that the sheet had a good function to release the cosmetic preparation toward the skin in use.

Example 8

In the same manner as in Example 1, the polypropylene resin was used to produce a meltblown nonwoven fabric sheet having a basis weight of 5 g/m².

Eighty (80) parts by mass of the rayon fiber and 20 parts by mass of the polyester fiber were blended uniformly, and then a semi-random card web having a basis weight of 40 g/m² was produced in the usual manner. The card web was placed on a punching drum support having an open area ratio of 25% and a hole diameter of 0.3 mm. The card web was continuously moved at a speed of 50 m/minute in a longitudinal direction thereof, and simultaneously subjected to a high-pressure water flow jet from above for entangling treatment to give an entangled fiber web (nonwoven fabric). In the entangling treatment, two nozzles (first and second nozzles) were used; where each nozzle had orifices arranged at an interval of 0.6 mm along the width direction (cross direction) of the web, each orifice had a hole diameter of 0.10 mm, and the distance between these nozzles were 20 cm. The water pressure of the high-pressure water flow jetted from the first nozzle was 3.0 MPa, and that from the second nozzle was 4.0 MPa. The previously produced meltblown nonwoven fabric sheet having a basis weight of 5 g/m² was unwound with a unwinding apparatus, and superposed on the web. The sheet and the web were placed on an entirely flat support having a finer mesh, and continuously moved, and simultaneously subjected to a high-pressure water flow jet for entangling treatment to entangle fibers constituting the two nonwoven fabrics and give combine these fabrics with each other. The entangling treatment was carried out using two nozzles, where each nozzle had orifices arranged at an interval of 0.6 mm along the width direction (cross direction) of the web, and each orifice had a hole diameter of 0.10 mm; and the water pressure of the high-pressure water flow from each nozzle was 5 MPa. Further, the resulting member was dried at 130° C. to give a combined nonwoven fabric having a basis weight of 45 g/m².

With respect to the resulting nonwoven fabric sheet, the thickness ratio was 1.0 of the liquid-retention layer relative to one (1) of the adhesion layer. Moreover, the fiber of the adhesion layer composed of the meltblown nonwoven fabric in the resulting nonwoven fabric sheet had a number-average fiber diameter of 2.57 μm and a standard deviation of fiber diameter distribution of 1.318, and the coefficient of fluctuation of the fiber diameter was 51.26%. Furthermore, in the resulting nonwoven fabric sheet, the liquid-retention layer had a void ratio of 92.7%, and the adhesion layer had a void ratio of 87.8%.

The sheet was impregnated with the cosmetic preparation, and the adhesion of the sheet was measured. The adhesion of the sheet impregnated with 900% by mass of the cosmetic preparation, which was an average initial impregnation rate of a typical facial mask sheet, was compared with the adhesion of the sheet impregnated with 500% by mass of the cosmetic preparation, which was modeled on the impregnation ratio in the state that the cosmetic preparation was consumed; and the adhesion of the sheet having an impregnation rate of 500% by mass was higher than that having an impregnation rate of 900% by mass. It was concluded from the results that the adhesion of the sheet was increased after use.

The adhesion feeling was evaluated by the sensory test, and all of five subjects judged the adhesion feeling to be "A". It was concluded from the results that the adhesion feeling is good in use. The cosmetic preparation releasability was not less than 10%. It was concluded from the results that the sheet had a good function to release the cosmetic preparation toward the skin in use.

Comparative Example 1

One hundred (100) parts by mass of the rayon fiber was opened uniformly, and then a semi-random card web having a basis weight of 60 g/m² was produced in the usual manner. The card web was placed on a punching drum support having an open area ratio of 25% and a hole diameter of 0.3 mm. The card web was continuously moved at a speed of 50 m/minute in a longitudinal direction thereof, and simultaneously subjected to a high-pressure water flow jet from above for entangling treatment to give an entangled fiber web (nonwoven fabric). In the entangling treatment, two nozzles (first and second nozzles) were used; where each nozzle had orifices arranged at an interval of 0.6 mm along the width direction (cross direction) of the web, each orifice had a hole diameter of 0.10 mm, and the distance between these nozzles were 20 cm. The water pressure of the high-pressure water flow jetted from the first nozzle was 3.0 MPa, and that from the second nozzle was 4.0 MPa. The web was placed on an entirely flat support having a finer mesh, and continuously moved, and simultaneously subjected to a high-pressure water flow jet for entangling treatment to entangle fibers. The entangling treatment was carried out using two nozzles, where each nozzle had orifices arranged at an interval of 0.6 mm along the width direction (cross direction) of the web, and each orifice had a hole diameter of 0.10 mm; and the water pressure of the high-pressure water flow from each nozzle was 5 MPa. Further, the resulting member was dried at 130° C. to give a spunlace nonwoven fabric having a basis weight of 60 g/m². The resulting nonwoven fabric sheet had a void ratio of 88.2%.

The sheet was impregnated with the cosmetic preparation, and the adhesion of the sheet was measured. The adhesion of the sheet having an impregnation rate of 500% by mass was lower than that having an impregnation rate of 900% by mass. It was concluded from the results that the adhesion of the sheet was lowered after use.

The adhesion feeling was evaluated by the sensory test, and all of five subjects judged the adhesion feeling to be "C". It was concluded from the results that the adhesion feeling is bad in use. The cosmetic preparation releasability was not less than 10%. It was concluded from the results that the sheet had a good function to release the cosmetic preparation toward the skin in use. However, it was concluded that the sheet was unsuitable for a facial mask sheet in a comprehensive manner.

Comparative Example 2

Forty (40) parts by mass of the rayon fiber and 60 parts by mass of the polyester fiber were blended uniformly, and then a semi-random card web having a basis weight of 60 g/m² was produced in the usual manner. The semi-random card web was subjected to entangling and drying treatments in the same manner as in Comparative Example 1 to give a spunlace nonwoven fabric having a basis weight of 60 g/m². The resulting nonwoven fabric sheet had a void ratio of 90.4%.

The sheet was impregnated with the cosmetic preparation, and the adhesion of the sheet was measured. The adhesion of the sheet having an impregnation rate of 500% by mass was lower than that having an impregnation rate of 900% by mass. It was concluded from the results that the adhesion of the sheet was lowered after use. The adhesion feeling was evaluated by the sensory test, and all of five subjects judged the adhesion feeling to be "C". It was concluded from the results that the adhesion feeling is bad in use. The cosmetic preparation releasability was not less than 10%. It was concluded from the results that the sheet had a good function to release the cosmetic preparation toward the skin in use. However, it was concluded that the sheet was unsuitable for a facial mask sheet in a comprehensive manner.

Comparative Example 3

One hundred (100) parts by mass of the cotton fiber was opened, and then a semi-random card web having a basis weight of 60 g/m² was produced in the usual manner. The semi-random card web was subjected to entangling and drying treatments in the same manner as in Comparative Example 1 to give a spunlace nonwoven fabric having a basis weight of 60 g/m². The resulting nonwoven fabric sheet had a void ratio of 90.2%.

The sheet was impregnated with the cosmetic preparation, and the adhesion of the sheet was measured. The adhesion of the sheet having an impregnation rate of 500% by mass was lower than that having an impregnation rate of 900% by mass. It was concluded from the results that the adhesion of the sheet was lowered after use.

The adhesion feeling was evaluated by the sensory test, and all of five subjects judged the adhesion feeling to be "C". It was concluded from the results that the adhesion feeling is bad in use. The cosmetic preparation releasability was not less than 10%. It was concluded from the results that the sheet had a good function to release the cosmetic preparation toward the skin in use. However, it was concluded that the sheet was unsuitable for a facial mask sheet in a comprehensive manner.

Comparative Example 4

One hundred (100) parts by mass of the rayon fiber was opened uniformly, and then a semi-random card web having a basis weight of 32 g/m² was produced in the usual manner. The card web was placed on a punching drum support having an open area ratio of 25% and a hole diameter of 0.3 mm. The card web was continuously moved at a speed of 50 m/minute in a longitudinal direction thereof, and simultaneously subjected to a high-pressure water flow jet from above for entangling treatment to give an entangled fiber web (nonwoven fabric). In the entangling treatment, two nozzles (first and second nozzles) were used; where each nozzle had orifices arranged at an interval of 0.6 mm along the width direction (cross direction) of the web, each orifice had a hole diameter of 0.10 mm, and the distance between these nozzles were 20 cm. The water pressure of the high-pressure water flow jetted from the first nozzle was 4.0 MPa, and that from the second nozzle was 5.0 MPa. The web was placed on an entirely flat support having a finer mesh, and continuously moved, and simultaneously subjected to a high-pressure water flow jet for entangling treatment to entangle fibers. The entangling treatment was carried out using two nozzles, where each nozzle had orifices arranged at an interval of 0.6 mm along the width direction (cross direction) of the web, and each orifice had a hole diameter of 0.10 mm; and the water pressure of the high-pressure water flow from each nozzle was 5 MPa. Further, the resulting member was dried at 130° C. to give a spunlace nonwoven fabric having a basis weight of 32 g/m².

Next, 100 parts by mass of the split fiber was opened uniformly, and then semi-random card webs, each having a basis weight of 24 g/m², were individually produced from two cards in the usual manner. The two card webs and the previously produced spunlace nonwoven fabric were laminated so that the spunlace nonwoven fabric might be interposed between the card webs. The laminate was placed on a punching drum support having an open area ratio of 25% and a hole diameter of 0.3 mm. The laminate was continuously moved at a speed of 50 m/minute in a longitudinal direction thereof, and simultaneously subjected to a high-pressure water flow jet from above for entangling treatment to give an entangled laminated fiber web (laminated nonwoven fabric). In the entangling treatment, two nozzles (first and second nozzles) were used; where each nozzle had orifices arranged at an interval of 0.6 mm along the width direction (cross direction) of the web, each orifice had a hole diameter of 0.10 mm, and the distance between these nozzles were 20 cm. The water pressure of the high-pressure water flow jetted from the first nozzle was 3.0 MPa, and that from the second nozzle was 4.0 MPa. The web was placed on an entirely flat support having a finer mesh, and continuously moved, and simultaneously subjected to a high-pressure water flow jet for entangling treatment to entangle fibers. The entangling treatment was carried out using two nozzles, where each nozzle had orifices arranged at an interval of 0.6 mm along the width direction (cross direction) of the web, and each orifice had a hole diameter of 0.10 mm; and the water pressure of the high-pressure water flow from each nozzle was 5 MPa. Further, the resulting member was dried at 130° C. to give a laminated spunlace nonwoven fabric having a basis weight of 80 g/m². The resulting nonwoven fabric sheet had a void ratio of 86.8%.

The sheet was poorly impregnated with the cosmetic preparation, and it took a time to complete the impregnation of the sheet with the cosmetic preparation. The adhesion of the sheet was measured, and the adhesion of the sheet having an impregnation rate of 500% by mass was slightly lower than that having an impregnation rate of 900% by mass. It was concluded from the results that the adhesion of the sheet was slightly lowered after use.

The adhesion feeling was evaluated by the sensory test, and four subjects judged the adhesion feeling to be "B", and one subject judged to be "C". It was concluded from the results that the adhesion feeling varied and showed a bad tendency in use. The cosmetic preparation releasability was not less than 10%. It was concluded from the results that the sheet had a good function to release the cosmetic preparation toward the skin in use. However, it was concluded that the sheet was unsuitable for a facial mask sheet in a comprehensive manner.

Comparative Example 5

In the same manner as in Example 3 except that the poly (butylene terephthalate) resin (MFR=90 g) was used and that the air pressure was 0.4 MPa, a meltblown nonwoven fabric sheet having a basis weight of 20 g/m$^2$ was produced.

In the same manner as in Example 3, 40 parts by mass of the rayon fiber and 60 parts by mass of the polyester fiber were used to produce an entangled fiber web (nonwoven fabric). The previously produced meltblown nonwoven fabric sheet having a basis weight of 20 g/m$^2$ was unwound with a unwinding apparatus, and superposed on the web. The entangle and drying treatments were carried out in the same manner as in Example 3, and a combined nonwoven fabric having a basis weight of 80 g/m$^2$ was obtained.

With respect to the resulting nonwoven fabric sheet, the thickness ratio was 2.2 of the liquid-retention layer relative to one (1) of the adhesion layer. Moreover, the fiber of the adhesion layer composed of the meltblown nonwoven fabric in the resulting nonwoven fabric sheet had a number-average fiber diameter of 17.15 μm and a standard deviation of fiber diameter distribution of 6.127, and the coefficient of fluctuation of the fiber diameter was 35.72%. Furthermore, in the resulting nonwoven fabric sheet, the liquid-retention layer had a void ratio of 90.8%, and the adhesion layer had a void ratio of 92.7%.

The sheet was impregnated with the cosmetic preparation, and the adhesion of the sheet was measured. The adhesion of the sheet having an impregnation rate of 500% by mass was lower than that having an impregnation rate of 900% by mass. It was concluded from the results that the adhesion of the sheet was lowered after use.

The adhesion feeling was evaluated by the sensory test, and all of five subjects judged the adhesion feeling to be "C". It was concluded from the results that the adhesion feeling was bad in use. The cosmetic preparation releasability was not less than 10%. It was concluded from the results that the sheet had a good function to release the cosmetic preparation toward the skin in use. However, it was concluded that the sheet was unsuitable for a facial mask sheet in a comprehensive manner.

Comparative Example 6

Forty (40) parts by mass of the rayon fiber and 60 parts by mass of the polyester fiber were blended uniformly, and then a semi-random card web having a basis weight of 60 g/m$^2$ was produced in the usual manner. The card web was placed on a punching drum support having an open area ratio of 25% and a hole diameter of 0.3 mm. The card web was continuously moved at a speed of 50 m/minute in a longitudinal direction thereof, and simultaneously subjected to a high-pressure water flow jet from above for entangling treatment to give an entangled fiber web (nonwoven fabric). In the entangling treatment, two nozzles (first and second nozzles) were used; where each nozzle had orifices arranged at an interval of 0.6 mm along the width direction (cross direction) of the web, each orifice had a hole diameter of 0.10 mm, and the distance between these nozzles were 20 cm. The water pressure of the high-pressure water flow jetted from the first nozzle was 3.0 MPa, and that from the second nozzle was 4.0 MPa. The web was placed on an entirely flat support having a finer mesh, and continuously moved, and simultaneously subjected to a high-pressure water flow jet for entangling treatment to entangle fibers constituting the web. The entangling treatment was carried out using two nozzles, where each nozzle had orifices arranged at an interval of 0.6 mm along the width direction (cross direction) of the web, and each orifice had a hole diameter of 0.10 mm; and the water pressure of the high-pressure water flow from each nozzle was 5 MPa. Further, the resulting member was dried at 130° C. to give a spunlace nonwoven fabric having a basis weight of 60 g/m$^2$.

The resulting spunlace nonwoven fabric was bonded to the polyester film having a thickness of 12 μm with the adhesive resin extruded through a T-die to give a combined nonwoven fabric having a basis weight of 91 g/m$^2$.

With respect to the resulting nonwoven fabric sheet, the thickness ratio was 13.7 of the liquid-retention layer relative to one (1) of the film layer. Moreover, in the resulting nonwoven fabric sheet, the liquid-retention layer had a void ratio of 88.7%, and the film layer had a void ratio of 0%.

The sheet was impregnated with the cosmetic preparation, and the adhesion of the sheet was measured. The adhesion of the sheet having an impregnation rate of 500% by mass was higher than that having an impregnation rate of 900% by mass. It was concluded from the results that the adhesion of the sheet was increased after use.

The adhesion feeling was evaluated by the sensory test, and all of five subjects judged the adhesion feeling to be "C" because the film inhibited the conformity to the skin. It was concluded from the results that the adhesion feeling is bad in use. The cosmetic preparation releasability was less than 10%. It was concluded from the results that the sheet had a bad function to release the cosmetic preparation toward the skin in use. It was concluded that the sheet was unsuitable for a facial mask sheet in a comprehensive manner.

Comparative Example 7

The combined nonwoven fabric having a basis weight of 91 g/m$^2$ obtained in Comparative Example 6 was pricked with a metal needle from the film layer side of the fabric to give through-bores (or through-holes), each having a diameter of about 900 μm, at intervals of 2 cm over the whole surface thereof. With respect to the resulting nonwoven fabric sheet, the thickness ratio was 14.2 of the liquid-retention layer relative to one (1) of the film layer. Moreover, in the resulting nonwoven fabric sheet, the liquid-retention layer had a void ratio of 89.0%, and the film layer had a void ratio of 0.2%.

The sheet was impregnated with the cosmetic preparation, and the adhesion of the sheet was measured. The adhesion of the sheet having an impregnation rate of 500% by mass was higher than that having an impregnation rate of 900% by mass. It was concluded from the results that the adhesion of the sheet was increased after use.

The adhesion feeling was evaluated by the sensory test, and all of five subjects judged the adhesion feeling to be "C" because the film inhibited the conformity to the skin. It was concluded from the results that the adhesion feeling is bad in use. The cosmetic preparation releasability was less than 10%. It was concluded from the results that the sheet had a bad function to release the cosmetic preparation toward the skin in use. It was concluded that the sheet was unsuitable for a facial mask sheet in a comprehensive manner.

Comparative Example 8

The combined nonwoven fabric having a basis weight of 91 g/m² obtained in Comparative Example 6 was pricked with a metal needle from the film layer side of the fabric to give through-bores (or through-holes), each having a diameter of about 900 μm, at intervals of 1 cm over the whole surface thereof. With respect to the resulting nonwoven fabric sheet, the thickness ratio was 14.4 of the liquid-retention layer relative to one (1) of the film layer. Moreover, in the resulting nonwoven fabric sheet, the liquid-retention layer had a void ratio of 89.2%, and the film layer had a void ratio of 0.6%.

The sheet was impregnated with the cosmetic preparation, and the adhesion of the sheet was measured. The adhesion of the sheet having an impregnation rate of 500% by mass was higher than that having an impregnation rate of 900% by mass. It was concluded from the results that the adhesion of the sheet was increased after use.

The adhesion feeling was evaluated by the sensory test, and all of five subjects judged the adhesion feeling to be "C" because the film inhibited the conformity to the skin. It was concluded from the results that the adhesion feeling is bad in use. The cosmetic preparation releasability was less than 10%. It was concluded from the results that the sheet had a bad function to release the cosmetic preparation toward the skin in use. It was concluded that the sheet was unsuitable for a facial mask sheet in a comprehensive manner.

The results of Examples are summarized in Table 1, and the results of Comparative Examples are summarized in Table 2.

TABLE 1

| | | | Examples | | | | | | | |
|---|---|---|---|---|---|---|---|---|---|---|
| | | | 1 | 2 | 3 | 4 | 5 | 6 | 7 | 8 |
| Liquid-retention layer | Production process | | Spunlace | Spunlace | Spunlace | Spunlace | Spunlace | Steam jet | Spunlace | Spunlace |
| | Basis weight | | 60 g/m² | 40 g/m² | 60 g/m² | 80 g/m² | 60 g/m² | 100 g/m² | 95 g/m² | 40 g/m² |
| | Fiber A | Species | Rayon | Rayon | Rayon | Tencel | Rayon | Sheath-core conjugated | Rayon | Rayon |
| | | Fineness · Fiber length | 1.7 T × 40 mm | 1.7 T × 40 mm | 1.7 T × 40 mm | 1.7 T × 38 mm | 1.7 T × 40 mm | 2.2 T × 51 mm | 1.7 T × 40 mm | 1.7 T × 40 mm |
| | | Component ratio | 40% | 40% | 40% | 40% | 40% | 30% | 20% | 80% |
| | Fiber B | Species | Polyester | Polyester | Polyester | Sheath-core conjugated | Polyester | Polyester | Polyester | Polyester |
| | | Fineness · fiber length | 1.6 T × 51 mm | 1.6 T × 51 mm | 1.6 T × 51 mm | 2.2 T × 51 mm | 1.6 T × 51 mm | 1.6 T × 51 mm | 1.6 T × 51 mm | 1.6 T × 51 mm |
| | | Component ratio | 60% | 60% | 60% | 60% | 60% | 70% | 80% | 20% |
| | CAD web fiber orientation | | Semi-random | Semi-random | Semi-random | Semi-random | Semi-random | Semi-random | Semi-random | Semi-random |
| Adhesion layer | Production process | | Meltblown | Meltblown | Meltblown | Meltblown | Meltblown | Meltblown | Meltblown | Meltblown |
| | Basis weight | | 5 g/m² | 5 g/m² | 20 g/m² | 20 g/m² | 5 g/m² | 10 g/m² | 5 g/m² | 5 g/m² |
| | Resin | Species | PP | PP | PBT | EVOH | Urethane | Urethane | PP | PP |
| | | Component ratio | 100% | 100% | 100% | 100% | 100% | 100% | 100% | 100% |
| | | Average fiber diameter | 2.57 μm | 2.57 μm | 5.26 μm | 6.73 μm | 3.75 μm | 3.89 μm | 2.57 μm | 2.57 μm |
| | | Standard deviation | 1.318 | 1.318 | 1.504 | 2.813 | 2.253 | 2.482 | 1.318 | 1.318 |
| | | Coefficient of fluctuation | 51.26% | 51.26% | 28.59% | 41.81% | 60.08% | 63.79% | 51.26% | 51.26% |
| Combined member | Combination method | | Spunlace | Spunlace | Spunlace | Spunlace | Direct blown | Direct blown | Spunlace | Spunlace |
| | Basis weight | | 65 g/m² | 45 g/m² | 80 g/m² | 100 g/m² | 65 g/m² | 110 g/m² | 100 g/m² | 45 g/m² |
| | Thickness | Liquid-retention layer | 436 μm | 416 μm | 461 μm | 576 μm | 441 μm | 1129 μm | 932 μm | 389 μm |
| | | Adhesion layer | 41 μm | 48 μm | 81 μm | 110 μm | 31 μm | 42 μm | 46 μm | 45 μm |
| | Void ratio | Liquid-retention layer | 90.4% | 93.3% | 90.9% | 90.0% | 90.5% | 93.5% | 92.8% | 92.7% |
| | | Adhesion layer | 86.6% | 88.6% | 81.2% | 85.1% | 86.0% | 79.3% | 88.1% | 87.8% |
| | Water retention | | 1021% | 1033% | 1015% | 1014% | 1098% | 1315% | 1118% | 1233% |
| | Adhesion | 900% | 0.585 N | 0.533 N | 0.560 N | 0.550 N | 0.562 N | 0.560 N | 0.624 N | 0.523 N |
| | | 500% | 1.040 N | 1.094 N | 0.865 N | 0.873 N | 0.965 N | 1.165 N | 1.142 N | 0.994 N |
| | Adhesion feeling | | Good | Good | Good | Good | Good | Good | Good | Good |
| | Released quantity of cosmetic preparation | | 24.0% | 25.9% | 25.7% | 24.5% | 24.1% | 24.0% | 25.3% | 17.1% |
| | Stress at 50% elongation | | 3.7 N | 2.3 N | 3.9 N | 4.2 N | 3.4 N | 2.4 N | 5.7 N | 3.5 N |

TABLE 2

| | | Comparative Examples | | | | | | | |
|---|---|---|---|---|---|---|---|---|---|
| | | 1 | 2 | 3 | 4 | 5 | 6 | 7 | 8 |
| Liquid-retention layer | Production process | Spunlace | Spunlace | Spunlace | Spunlace | Spunlace | Spunlace | Spunlace | Spunlace |
| | Basis weight | 60 g/m² | 60 g/m² | 60 g/m² | 80 g/m² | 60 g/m² | 60 g/m² | 60 g/m² | 60 g/m² |
| | Fiber A Species | Regenerated cellulose | Regenerated cellulose | Cotton | Regenerated cellulose | Regenerated cellulose | Regenerated cellulose | Regenerated cellulose | Regenerated cellulose |
| | Fineness · fiber length | 1.7 T × 40 mm | 1.7 T × 40 mm | — | 1.7 T × 40 mm | 1.7 T × 40 mm | 1.7 T × 40 mm | 1.7 T × 40 mm | 1.7 T × 40 mm |
| | Component ratio | 100% | 40% | 100% | 40% (Central layer) | 40% | 40% | 40% | 40% |
| | Fiber B Species | — | Polyester | — | Split-fiber | Polyester | Polyester | Polyester | Polyester |
| | Fineness · fiber length | — | 1.6 T × 51 mm | — | 3.8 T × 51 mm | 1.6 T × 51 mm | 1.6 T × 51 mm | 1.6 T × 51 mm | 1.6 T × 51 mm |
| | Component ratio | — | 60% | — | 60% (both side layers) | 60% | 60% | 60% | 60% |
| | CAD web fiber orientation | Semi-random | Semi-random | Semi-random | Semi-random | Semi-random | Semi-random | Semi-random | Semi-random |
| Adhesion layer | Production process | — | — | — | — | Meltblown | Melt extrusion | Melt extrusion | Melt extrusion |
| | Basis weight | — | — | — | — | 20 g/m² | 31 g/m² | 31 g/m² | 31 g/m² |
| | Resin Species | — | — | — | — | PBT | PET | PET | PET |
| | Component ratio | — | — | — | — | 100% | 100% | 100% | 100% |
| | Average fiber diameter | — | — | — | — | 17.15 μm | — | — | — |
| | Standard deviation | — | — | — | — | 6.127 | — | — | — |
| | Coefficient of fluctuation | — | — | — | — | 35.72% | — | — | — |
| Combined member | Combination method | — | — | — | — | Spunlace | Extrusion lamination | Extrusion lamination | Extrusion lamination |
| | Basis weight | 60 g/m² | 60 g/m² | 60 g/m² | 80 g/m² | 80 g/m² | 91 g/m² | 91 g/m² | 91 g/m² |
| | Thickness Liquid-retention layer | 336 μm | 437 μm | 398 μm | 439 μm | 453 μm | 370 μm | 382 μm | 388 μm |
| | Adhesion layer | — | — | — | — | 210 μm | 27 μm | 27 μm | 27 μm |
| | Void ratio Liquid-retention layer | 88.2% | 90.4% | 90.2% | 86.8% | 90.8% | 88.7% | 89.0% | 89.2% |
| | Adhesion layer | — | — | — | — | 92.7% | 0% | 0.2% | 0.6% |
| | Water retention | 1314% | 1050% | 821% | 550% | 1105% | 611% | 632% | 618% |
| | Adhesion 900% | 0.578 N | 0.471 N | 0.544 N | 0.450 N | 0.488 N | 0.130 N | 0.122N | 0.119 N |
| | 500% | 0.140 N | 0.120 N | 0.020 N | 0.433 N | 0.158 N | 0.899 N | 0.902 N | 0.963 N |
| | Adhesion feeling | Bad | Bad | Bad | Slightlybad | Bad | Bad | Bad | Bad |
| | Released quantity of cosmetic preparation | 22.1% | 24.3% | 22.9% | 22.7% | 20.4% | 0.4% | 1.6% | 2.2% |
| | Stress at 50% elongation | 3.2 N | 3.1 N | 16.5 N | 3.7 N | 5.5 N | 115.3 N | 103.6 N | 88.3 N |

INDUSTRIAL APPLICABILITY

The laminated sheet of the present invention absorbs a liquid component and is available for an application for contacting with the skin, for example, a sheet for absorbing a body fluid (e.g., a surface material for a sanitary napkin or a diaper, a diaper liner, and a wet wipe), a skin care sheet (e.g., a facial mask sheet, a makeup-removing sheet), and a cleansing sheet or a body-washing sheet (e.g., a sweat-wiping sheet, an oil-blocking sheet, and a cooling sheet), and a medicated sheet (e.g., an itching-controlling sheet and a wet compress). In particular, the laminated sheet of the present invention is closely contacted with all sites of the human body, including a site sensitive to a stimulus and a site from which an applied sheet is easily peeled off by gravitation or depending on movement, and keeps a high wet state. Thus, the sheet is particularly useful for a mask impregnated with an effective component (such as a moisturizing or skin-whitening component for the entire face, nose, eyes, lip, neck, and others), a cleansing sheet for removing and wiping a makeup, a medicated or therapeutic sheet impregnated with a blood-circulation-promoting component or an itching-controlling component for skin, a cooling sheet impregnated with a volatile liquid, which uses the evaporation heat of the liquid for cooling, and others.

DESCRIPTION OF REFERENCE NUMERALS

10 . . . Sample (specimen)
11 . . . Table (acrylic board)
12 . . . Clip 13 ... Pulley
14 ... Polyamide yarn
15 ... Load cell

The invention claimed is:

1. A laminated sheet, comprising a liquid-retention layer, having an ability to absorb a liquid component, and an adhesion layer contactable with a skin,
wherein:
the liquid-retention layer comprises a first nonwoven structural member comprising a first fiber;
the adhesion layer is formed on at least one side of the liquid-retention layer and is permeable to the liquid component;
the adhesion layer comprises a second nonwoven structural member comprising a second fiber;
the second fiber has a number-average fiber diameter of 1 to 8 μm; and
a thickness ratio of the adhesion layer, relative to the liquid-retention layer, is 1/6 to 1/50 as a ratio of the adhesion layer/the liquid-retention layer and a thickness of the adhesion layer is 10 to 500 μm
wherein the first fiber has a fiber diameter larger than that of the second fiber and
wherein said liquid-retention layer and said adhesion layer are entangled by a spunlace method or directly blowing a fiber for said adhesion layer to said liquid-retention layer.

2. The laminated sheet of claim 1, wherein the second fiber has a standard deviation of fiber diameter of not more than 5.

3. The laminated sheet of claim 1, wherein the first fiber comprises a hydrophilic resin fiber, and the second fiber comprises a thermoplastic resin fiber.

4. The laminated sheet of claim 1, wherein the first fiber comprises a hydrophilic resin fiber in a proportion of less than 50% by mass of the liquid-retention layer, and the second fiber comprises at least one member selected from the group consisting of a polyester fiber, a polyolefin fiber, a poly(vinyl alcohol) fiber, and a polyurethane fiber.

5. The laminated sheet of claim 4, wherein the first fiber has a number-average fiber diameter of 9 to 32 μm.

6. The laminated sheet of claim 1, wherein the liquid-retention layer has a density of 0.03 to 0.20 g/cm$^3$ and a void ratio of not less than 80%, and the adhesion layer has a density of 0.05 to 0.35 g/cm$^3$ and a void ratio of not less than 70%.

7. The laminated sheet of claim 1, wherein the adhesion layer comprises a meltblown nonwoven fabric.

8. The laminated sheet of claim 1 having a stress at 50% elongation of 0.5 to 15 N/5 cm in at least one direction under wetting in accordance with JIS L 1913.

9. The laminated sheet of claim 1, which is impregnated with the liquid component.

10. The laminated sheet of claim 9, which is a skin care sheet comprising a cosmetic preparation as the liquid component.

11. The laminated sheet of claim 10, which is a facial mask sheet.

12. The laminated sheet of claim 1, further comprising a second adhesion layer formed on the liquid-retention layer.

13. The laminated sheet of claim 1, further comprising a nonporous film formed on the liquid-retention layer.

14. The laminated sheet of claim 1 having a frictional force of not less than 0.6 N when the sheet is impregnated with 500% by mass of a cosmetic preparation, relative to the mass of the sheet,
wherein
the frictional force of the sheet impregnated with 500% by mass of the cosmetic preparation is larger than that of a sheet impregnated with 900% by mass of the cosmetic preparation, relative to the mass of the sheet, and
the frictional force of each impregnated sheet is measured in accordance with ASTM-D1984.

15. A process for producing the laminated sheet of claim 1, the process comprising
(a) forming an adhesion layer by a meltblown method, and
(b) laminating the adhesion layer on at least one side of a liquid-retention layer comprising a nonwoven structural member,
wherein the laminating (b) comprises entangling the liquid-retention layer and the adhesion layer by a spunlace method or directly blowing a fiber for the adhesion layer to the liquid-retention layer.

16. The process of claim 15, wherein
the liquid-retention layer is formed by entangling a hydrophobic fiber and a hydrophilic fiber by a spunlace method.

17. The process of claim 15, wherein
the liquid-retention layer is produced by entangling and thermally bonding a hydrophobic fiber and a hydrophilic fiber comprising an ethylene-vinyl alcohol copolymer under moisture by a steam jet method.

18. A process, comprising contacting the laminated sheet of claim 1 with skin such that the adhesion layer is in contact with the skin, wherein the laminated sheet has been impregnated with the liquid component.

* * * * *